US006936584B1

(12) United States Patent  
Beeley et al.

(10) Patent No.: US 6,936,584 B1  
(45) Date of Patent: Aug. 30, 2005

(54) MIXED AMYLIN ACTIVITY COMPOUNDS

(75) Inventors: Nigel R. A. Beeley, Solana Beach, CA (US); Kathryn Prickett, San Diego, CA (US); Kevin Beaumont, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/622,104

(22) PCT Filed: Feb. 5, 1999

(86) PCT No.: PCT/US99/02603

§ 371 (c)(1),  
(2), (4) Date: Jul. 17, 2001

(87) PCT Pub. No.: WO99/40928

PCT Pub. Date: Aug. 19, 1999

Related U.S. Application Data

(60) Provisional application No. 60/074,746, filed on Feb. 13, 1998.

(51) Int. Cl.$^7$ ............................ A61K 37/02; C07K 7/10
(52) U.S. Cl. ......................... 514/12; 514/866; 530/324
(58) Field of Search ........................... 530/324; 514/12, 514/866

(56) References Cited

U.S. PATENT DOCUMENTS

| | | |
|---|---|---|
| 4,758,550 A | 7/1988 | Cardinaux et al. |
| 5,124,314 A | 6/1992 | Cooper |
| 5,175,145 A | 12/1992 | Cooper |
| 5,264,372 A | 11/1993 | Beaumont et al. |
| 5,266,561 A | 11/1993 | Cooper et al. |
| 5,321,008 A | 6/1994 | Beaumont et al. |
| 5,367,052 A | 11/1994 | Cooper et al. |
| 5,376,638 A | * 12/1994 | Young et al. .............. 514/12 |
| 5,508,260 A | 4/1996 | Beaumont et al. |
| 5,580,953 A | 12/1996 | Albrecht et al. |
| 5,625,032 A | 4/1997 | Gaeta et al. |
| 5,686,411 A | 11/1997 | Gaeta et al. |
| 5,795,861 A | 8/1998 | Kolterman et al. |

FOREIGN PATENT DOCUMENTS

| | | |
|---|---|---|
| WO | WO 92/11863 | 7/1992 |
| WO | WO 93/10147 | 5/1993 |
| WO | WO 93/14408 | 7/1993 |
| WO | WO 95/07098 | 3/1995 |

OTHER PUBLICATIONS

Alam et al. Biochem. Biophys. Res. Commun. 179(1):134–139 (1991).
Azria et al., Calcitonins–Physiological and Pharmacological Aspects, pp. 24–25 New York: Springer–Verlag (1989).
Beaumont et al., British Journal of Pharmacology, 115(5):713–715 (1995).
Brain et al., Eur. Journal of Pharmacol., 183:2221 (1990).
Broderick et al., Biochem. Biophys. Res. Comm., 177:932–938 (1991).
Brown et al., Diabetes 43: 172A Abstract #536 (1994).
Chance et al., Brain Res., 539: 352–354 (1991).
Chantry et al., Biochem. J., 277:139–143 (1991).
Cooper et al., Proc. Natl. Acad. Sci., USA, 84:8628–8632 (1987).
Cooper et al., Proc. Natl. Acad. Sci., 85:7763–7766 (1988).
Fineman et al., Diabetes 40:30A Abstract #0117 (1997).
Follett et al., Clinical Research, 39(1):39A (1991).
Gaeta et al., Med. Chem. Res., 3:483–490 (1990).
Gamse et al., J. of Bone and Mineral Research, 8 (Suppl 1):S200 (1993) Abstract #334.
Gedulin et al., Biochem. Biophys. Res. Commun., 180(2):782–789 (1991).
Gedulin et al., Diabetologia 38 (Suppl 1):A244 Abstract #945 (1995).
Gedulin et al., Metabolism 46(1):67–70 (1997).
Gomez–Foix et al., Biochem J. 276:607–610 (1991).
Huang et al., Hypertension 19:I–101–I–109 (1992).
Jonderko K et al., J. of Clinical Gastroenterology 1990 United States, 12(1), 22–28 (1990).
Koda et al., The Lancet, 339:1179–1180 (1992).
Kolterman et al., Diabetologia, 39:492–499 (1996).
Koopmans et al., Diabetologia, 34:218–224 (1991).
Leighton and Cooper, Nature, 335:632–635 (1988).
Lupien and Young, Diabetes Nutrition and Metabolism–Clinical and Experimental, 6(1) 13–18 (Feb. 1993).
MacDonald et al., Diabetologia, 38(1):118 (1995) (abstract).
Molina et al., Diabetes, 39:260–265 (1990).
Moore et al., Biochem. Biophys. Res. Commun., 179(1):1–9 (1991).
Munson, Anal. Biochem., 107:220–239 (1980).
Nowak et al., J. Lab. Clin. Med., 123(1):110–116 (1994).
Nyholm et al., J. of Clinical Endocrinology and Metabolism, 81(3):1083–1089 (1996).
Ogawa et al., J. Clin. Invest., 85: 973–976 (1990).
Pittner et al., FEBS Letters, 365(1):98–100 (1995).
Pittner et al., J. of Cellular Biochemistry, 55S:19–28 (1994).
Plourde et al., Life Sci., 52:857–862 (1993).
Pozvek, Gordana et al., Molecular Pharmacology, 51(4), 658–665 (1997).

(Continued)

*Primary Examiner*—Bennett Celsa  
(74) *Attorney, Agent, or Firm*—Arnold & Porter LLP

(57) ABSTRACT

Compounds which inhibit certain activities of amylin but which also act as amylin agonists with respect to other amylin activities are disclosed. Such compounds are useful in treating disturbances in fuel metabolism in mammals, including but not limited to, diabetes, mellitus, including Type I diabetes and Type II diabetes, impaired glucose tolerance, insulin resistance and Syndrome X. The present invention also relates to methods of treating Type I diabetes, beneficially regulating gastrointestinal motility, treating impaired glucose tolerance, treating postprandial hyperglycemia, treating obesity and treating Syndromne X, comprising administration of a therapeutically effective amount of certain compounds, as described herein.

25 Claims, 17 Drawing Sheets

OTHER PUBLICATIONS

Prickett et al., Petides: Chemistry, Structure and Biology, Proc. of the 14th Am. Peptide Symp., Jun. 1995, Columbus, OH/ed. Kaumaya, P.T.P., Hodges, R.S. pp. 620–622 (1996).
Scarpignato et al., Arch. int. Pharmacodyn. 246:286–294 (1980).
Silvestre et al., Reg. Pegt., 31:23–31 (1990).
Stephens et al., Diabetes, 40:395–400 (1991).
Van Valen et al., Neuroscience Letters, 119:195–198 (1990).
Wang et al., FEBS Lett., 291:195–198 (1991).
Wang et al., Technical Report No. 10, Supp. 42:28 (1988).
Young et al., Current Opinion in Endocrinology & Diabetes, 4(4):282–290 (1997).
Young et al., Mol. Cell. Endocrinol., 84:R1–R5 (1992).
Young et al., Am. J. Physiolog., 263(2):E274–E281 (1992).
Young et al., Am. J. of Physiology, 259:457–461 (1990).
Young et al., Diabetologia, 38:642–648 (1995).
Zaidi et al., Trends in Endocrinology and Metabolism, 4(8):255–259 (1993).
Zhu et al., Biochem. Biophys. Res. Commun., 177(2):771–776 (1991).

* cited by examiner

COMPOUNDS OF THE FORMULA: $X_1$-$X_2$-$X_3$-Leu-$X_4$-Glu-Leu-$X_5$-$X_6$-Leu-Gln-Thr-Tyr-Pro-Arg-Thr-Asn-$X_7$-$NH_2$

| CPD. & SEQ. ID.NO. | $X_1$ | $X_2$ | $X_3$ | Leu | $X_4$ | Glu Leu | $X_5$ | $X_6$ | Leu Gln Thr Tyr Pro Arg Thr Asn | $X_7$ | $NH_2$ |
|---|---|---|---|---|---|---|---|---|---|---|---|
| 1 | Leu Ser Thr Cys Val Leu | Gly | Arg | Leu | Ser Gln | Glu Leu | His | Arg | Leu Gln Thr Tyr Pro Arg Thr Asn | Thr Gly Ser Asn Thr Tyr | $NH_2$ |
| 2 | 4-methylpentanoyl Ser Thr Ala Val Leu | Aib | Lys(For) | Leu | Ser Gln | Glu Leu | Aib | Lys(For) | Leu Gln Thr Tyr Pro Arg Thr Asn | Thr Gly Ser Gly Thr Pro | $NH_2$ |
| 3 | Ac-Leu Ser Thr Ser Val Leu | Gly | Arg | Leu | Ser Gln | Glu Leu | His | Arg | Leu Gln Thr Tyr Pro Arg Thr Asn | Thr Gly Ser Asn Thr Tyr | $NH_2$ |
| 4 | Leu Ser Thr Ala Val Leu | Gly | Arg | Leu | Ser Gln | Glu Leu | His | Arg | Leu Gln Thr Tyr Pro Arg Thr Asn | Thr Gly Ser Asn Thr Tyr | $NH_2$ |
| 5 | Leu Ser Thr Ser Val Leu | Gly | Arg | Leu | Ser Gln | Glu Leu | His | Arg | Leu Gln Thr Tyr Pro Arg Thr Asn | Thr Gly Ser Asn Thr Tyr | $NH_2$ |
| 6 | Ac-Leu Ser Thr Ala Val Leu | Gly | Arg | Leu | Ser Gln | Glu Leu | His | Arg | Leu Gln Thr Tyr Pro Arg Thr Asn | Thr Gly Ser Asn Thr Tyr | $NH_2$ |
| 7 | Ac-Leu Ser Thr Cys Val Leu | Gly | Arg | Leu | Ser Gln | Glu Leu | His | Arg | Leu Gln Thr Tyr Pro Arg Thr Asn | Thr Gly Ser Asn Thr Tyr | $NH_2$ |
| 8 | Val Leu | Aib | Lys(For) | Leu | Ser Gln | Glu Leu | Aib | Lys(For) | Leu Gln Thr Tyr Pro Arg Thr Asn | Thr Gly Ser Asn Thr Tyr | $NH_2$ |
| 9 | Ac-Val Leu | Aib | Lys(For) | Leu | Ser Gln | Glu Leu | Aib | Lys(For) | Leu Gln Thr Tyr Pro Arg Thr Asn | Thr Gly Ser Asn Thr Tyr | $NH_2$ |
| 10 | 4-methylpentanoyl Ser Thr Ala Val Leu | Aib | Lys(For) | Leu | Ser Gln | Glu Leu | Aib | Lys(For) | Leu Gln Thr Tyr Pro Arg Thr Asn | Thr Gly Ser Asn Thr Tyr | $NH_2$ |
| 11 | 4-methylpentanoyl Ser Thr Cys Val Leu | Aib | Lys(For) | Leu | Ala Asn | Glu Leu | Aib | Lys(For) | Leu Gln Thr Tyr Pro Arg Thr Asn | Thr Gly Ser Asn Thr Tyr | $NH_2$ |
| 12 | Ala Thr | Aib | Lys(For) | Leu | Ala Asn | Glu Leu | Aib | Lys(For) | Leu Gln Thr Tyr Pro Arg Thr Asn | Thr Gly Ser Asn Thr Tyr | $NH_2$ |
| 13 | (Ac-)Ala Thr | Aib | Lys(For) | Leu | Ala Asn | Glu Leu | Aib | Lys(For) | Leu Gln Thr Tyr Pro Arg Thr Asn | Thr Gly Ser Asn Thr Tyr | $NH_2$ |

FIG. 8

COMPOUNDS OF THE FORMULA: $X_1-X_2-X_3$-Leu-$X_4$-Glu-Leu-$X_5-X_6$-Leu-Gln-Thr-Tyr-Pro-Arg-Thr-Asn-$X_7$-$NH_2$:

| SEQ. ID.NO. | $X_1$ | $X_2$ | $X_3$ | Leu | $X_4$ | Glu Leu | $X_5$ | $X_6$ | Leu Gln Thr Tyr Pro Arg Thr Asn | $X_7$ | $NH_2$ |
|---|---|---|---|---|---|---|---|---|---|---|---|
| 14 | Leu Ser Thr Cys Val Leu | Gly | Lys | Leu | Ser Gln | Glu Leu | His | Lys | Leu Gln Thr Tyr Pro Arg Thr Asn | Thr Gly Ser Gly Thr Pro | $NH_2$ |
| 15 | Val Leu | Gly | Lys | Leu | Ser Gln | Glu Leu | His | Lys | Leu Gln Thr Tyr Pro Arg Thr Asn | Thr Gly Ser GlyTyr Pro | $NH_2$ |
| 16 | Val Leu | Gly | Lys | Leu | Ser Gln | Glu Leu | His | Lys | Leu Gln Thr Tyr Pro Arg Thr Asn | Thr Gly Ser Asn Thr Tyr | $NH_2$ |
| 17 | (AcHN) Val Leu | Gly | Lys | Leu | Ser Gln | Glu Leu | His | Lys | Leu Gln Thr Tyr Pro Arg Thr Asn | Thr Gly Ser Asn Thr Tyr | $NH_2$ |
| 18 | Ac- Leu Ser Thr Ala Val Leu | Gly | Lys | Leu | Ser Gln | Glu Leu | His | Lys | Leu Gln Thr Tyr Pro Arg Thr Asn | Thr Gly Ser Gly Thr Pro | $NH_2$ |
| 19 | Ac- Leu Ser Thr Ala Val Leu | Gly | Lys | Leu | Ser Gln | Glu Leu | Aib | Lys | Leu Gln Thr Tyr Pro Arg Thr Asn | Thr Gly Ser Gly Thr Pro | $NH_2$ |
| 20 | Isocaproyl Ser Thr Ala Val Leu | Gly | Lys | Leu | Ser Gln | Glu Leu | His | Lys | Leu Gln Thr Tyr Pro Arg Thr Asn | Thr Gly Ser Gly Thr Pro | $NH_2$ |
| 21 | H Leu Ser Thr Ala Val Leu | Gly | Lys | Leu | Ser Gln | Glu Leu | His | Lys | Leu Gln Thr Tyr Pro Arg Thr Asn | Thr Gly Ser Gly Thr Pro | $NH_2$ |
| 22 | Adamantacetyl Ser Thr Ala Val Leu | Gly | Lys | Leu | Ser Gln | Glu Leu | His | Lys | Leu Gln Thr Tyr Pro Arg Thr Asn | Thr Gly Ser Gly Thr Pro | $NH_2$ |
| 23 | $CH_3CO$ Ser Thr Ala Val Leu | Gly | Lys | Leu | Ser Gln | Glu Leu | His | Lys | Leu Gln Thr Tyr Pro Arg Thr Asn | Thr Gly Ser Gly Thr Pro | $NH_2$ |
| 24 | Cyclohexylpropionyl Ser Thr Ala Val Leu | Gly | Lys | Leu | Ser Gln | Glu Leu | His | Lys | Leu Gln Thr Tyr Pro Arg Thr Asn | Thr Gly Ser Gly Thr Pro | $NH_2$ |
| 25 | Cyclopentyl C(O) Ser Thr Ala Val Leu | Gly | Lys | Leu | Ser Gln | Glu Leu | His | Lys | Leu Gln Thr Tyr Pro Arg Thr Asn | Thr Gly Ser Gly Thr Pro | $NH_2$ |
| 26 | Decanoyl Ser Thr Ala Val Leu | Gly | Lys | Leu | Ser Gln | Glu Leu | His | Lys | Leu Gln Thr Tyr Pro Arg Thr Asn | Thr Gly Ser Gly Thr Pro | $NH_2$ |

*FIG. 9*

SEQUENCE LISTING

<160> NUMBER OF SEQ ID NOS: 32

<210> SEQ ID NO 1
<211> LENGTH: 29

```
<212> TYPE: PRT
<213> ORGANISM: Artificial Sequence
<220> FEATURE:
<223> OTHER INFORMATION: Synthetic peptides

<400> SEQUENCE: 1

Leu Ser Thr Cys Val Leu Gly Arg Leu Ser Gln Glu Leu His Arg
 1               5                  10                  15

Leu Gln Thr Tyr Pro Arg Thr Asn Thr Gly Ser Asn Thr Tyr
                20                  25

<210> SEQ ID NO 2
<211> LENGTH: 29
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (1)
<223> OTHER INFORMATION: Xaa stands for 4-methylpentanoyl
<220> FEATURE:
<221> NAME/KEY: Amidation
<222> LOCATION: (7 and 14)
<223> OTHER INFORMATION: Xaa stands for Aib

<400> SEQUENCE: 2

Xaa Ser Thr Ala Val Leu Xaa Lys Leu Ser Gln Glu Leu Xaa Lys
 1               5                  10                  15

Leu Gln Thr Tyr Pro Arg Thr Asn Thr Gly Ser Gly Thr Pro
                20                  25

<210> SEQ ID NO 3
<211> LENGTH: 30
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (1 )
<223> OTHER INFORMATION: Xaa stands for Acetylation

<400> SEQUENCE: 3

Xaa Leu Ser Thr Ser Val Leu Gly Arg Leu Ser Gln Glu Leu His
 1               5                  10                  15

Arg Leu Gln Thr Tyr Pro Arg Thr Asn Thr Gly Ser Asn Thr Tyr
                20                  25                  30

<210> SEQ ID NO 4
<211> LENGTH: 29
<212> TYPE: PRT
<213> ORGANISM: Artificial Sequence
<220> FEATURE:
<223> OTHER INFORMATION: Synthetic peptides

<400> SEQUENCE: 4

Leu Ser Thr Ala Val Leu Gly Arg Leu Ser Gln Glu Leu His Arg
 1               5                  10                  15

Leu Gln Thr Tyr Pro Arg Thr Asn Thr Gly Ser Asn Thr Tyr
                20                  25

<210> SEQ ID NO 5
<211> LENGTH: 29
<212> TYPE: PRT
<213> ORGANISM: Artificial Sequence
<220> FEATURE:
```

<223> OTHER INFORMATION: Synthetic peptides

<400> SEQUENCE: 5

Leu Ser Thr Ser Val Leu Gly Arg Leu Ser Gln Glu Leu His Arg
 1               5                  10                  15

Leu Gln Thr Tyr Pro Arg Thr Asn Thr Gly Ser Asn Thr Tyr
            20                  25

<210> SEQ ID NO 6
<211> LENGTH: 30
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (1 )
<223> OTHER INFORMATION: Xaa stands for Acetylation

<400> SEQUENCE: 6

Xaa Leu Ser Thr Ala Val Leu Gly Arg Leu Ser Gln Glu Leu His
 1               5                  10                  15

Arg Leu Gln Thr Tyr Pro Arg Thr Asn Thr Gly Ser Asn Thr Tyr
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (1 )
<223> OTHER INFORMATION: Xaa stands for Acetylation

<400> SEQUENCE: 7

Xaa Leu Ser Thr Cys Val Leu Gly Arg Leu Ser Gln Glu Leu His
 1               5                  10                  15

Arg Leu Gln Thr Tyr Pro Arg Thr Asn Thr Gly Ser Asn Thr Tyr
            20                  25                  30

<210> SEQ ID NO 8
<211> LENGTH: 25
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (3 and 10 )
<223> OTHER INFORMATION: Xaa stands for Acetylation

<400> SEQUENCE: 8

Val Leu Xaa Lys Leu Ser Gln Glu Leu Xaa Lys Leu Gln Thr Tyr
 1               5                  10                  15

Pro Arg Thr Asn Thr Gly Ser Asn Thr Tyr
            20                  25

<210> SEQ ID NO 9
<211> LENGTH: 26
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation

```
<222> LOCATION: (1 )
<223> OTHER INFORMATION: Xaa stands for Acetylation
<220> FEATURE:
<221> NAME/KEY: Amidation
<222> LOCATION: (4 and 11 )
<223> OTHER INFORMATION: Xaa stands for Aib

<400> SEQUENCE: 9

Xaa Val Leu Xaa Lys Leu Ser Gln Glu Leu Xaa Lys Leu Gln Thr
 1               5                  10                  15

Tyr Pro Arg Thr Asn Thr Gly Ser Asn Thr Tyr
                20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (1)
<223> OTHER INFORMATION: Xaa stands for 4-methylpentanoyl
<220> FEATURE:
<221> NAME/KEY: Amidation
<222> LOCATION: (7 and 14)
<223> OTHER INFORMATION: Xaa stands for Aib

<400> SEQUENCE: 10

Xaa Ser Thr Ala Val Leu Xaa Lys Leu Ser Gln Glu Leu Xaa Lys
 1               5                  10                  15

Leu Gln Thr Tyr Pro Arg Thr Asn Thr Gly Ser Asn Thr Tyr
                20                  25

<210> SEQ ID NO 11
<211> LENGTH: 29
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (1)
<223> OTHER INFORMATION: Xaa stands for 4-methylpentanoyl
<220> FEATURE:
<221> NAME/KEY: Amidation
<222> LOCATION: (7 and 14)
<223> OTHER INFORMATION: Xaa stands for Aib

<400> SEQUENCE: 11

Xaa Ser Thr Cys Val Leu Xaa Lys Leu Ser Gln Glu Leu Xaa Lys
 1               5                  10                  15

Leu Gln Thr Tyr Pro Arg Thr Asn Thr Gly Ser Asn Thr Tyr
                20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (3 and 10)
<223> OTHER INFORMATION: Xaa stands for Aib

<400> SEQUENCE: 12

Ala Thr Xaa Lys Leu Ala Asn Glu Leu Xaa Lys Leu Gln Thr Tyr
 1               5                  10                  15
```

Pro Arg Thr Asn Thr Gly Ser Asn Thr Tyr
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (1)
<223> OTHER INFORMATION: Xaa stands for Acetylation
<220> FEATURE:
<221> NAME/KEY: Amidation
<222> LOCATION: (3 and 10)
<223> OTHER INFORMATION: Xaa stands for Aib

<400> SEQUENCE: 13

Xaa Thr Xaa Lys Leu Ala Asn Glu Leu Xaa Lys Leu Gln Thr Tyr
1               5                   10                  15

Pro Arg Thr Asn Thr Gly Ser Asn Thr Tyr
            20                  25

<210> SEQ ID NO 14
<211> LENGTH: 29
<212> TYPE: PRT
<213> ORGANISM: Artificial Sequence
<220> FEATURE:
<223> OTHER INFORMATION: Salmon Calcitonin

<400> SEQUENCE: 14

Leu Ser Thr Cys Val Leu Gly Lys Leu Ser Gln Glu Leu His Lys
1               5                   10                  15

Leu Gln Thr Tyr Pro Arg Thr Asn Thr Gly Ser Gly Thr Pro
            20                  25

<210> SEQ ID NO 15
<211> LENGTH: 25
<212> TYPE: PRT
<213> ORGANISM: Artificial Sequence
<220> FEATURE:
<223> OTHER INFORMATION: Salmon Calcitonin

<400> SEQUENCE: 15

Val Leu Gly Lys Leu Ser Gln Glu Leu His Lys Leu Gln Thr Tyr
1               5                   10                  15

Pro Arg Thr Asn Thr Gly Ser Gly Thr Pro
            20                  25

<210> SEQ ID NO 16
<211> LENGTH: 25
<212> TYPE: PRT
<213> ORGANISM: Artificial Sequence
<220> FEATURE:
<223> OTHER INFORMATION: Salmon Calcitonin

<400> SEQUENCE: 16

Val Leu Gly Lys Leu Ser Gln Glu Leu His Lys Leu Gln Thr Tyr
1               5                   10                  15

Pro Arg Thr Asn Thr Gly Ser Asn Thr Tyr
            20                  25

<210> SEQ ID NO 17
<211> LENGTH: 25

```
<212> TYPE: PRT
<213> ORGANISM: Artificial Sequence
<220> FEATURE:
<223> OTHER INFORMATION: Salmon Calcitonin

<400> SEQUENCE: 17

Val Leu Gly Lys Leu Ser Gln Glu Leu His Lys Leu Gln Thr Tyr
1               5                   10                  15

Pro Arg Thr Asn Thr Gly Ser Asn Thr Tyr
                20                  25

<210> SEQ ID NO 18
<211> LENGTH: 30
<212> TYPE: PRT
<213> ORGANISM: Artificial Sequence
<220> FEATURE:
<223> OTHER INFORMATION: Salmon Calcitonin
<220> FEATURE:
<221> NAME/KEY: Amidation
<222> LOCATION: (1)
<223> OTHER INFORMATION: Xaa stands for Acetylation

<400> SEQUENCE: 18

Xaa Leu Ser Thr Ala Val Leu Gly Lys Leu Ser Gln Glu Leu His
1               5                   10                  15

Lys Leu Gln Thr Tyr Pro Arg Thr Asn Thr Gly Ser Gly Thr Pro
                20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Salmon Calcitonin
<220> FEATURE:
<221> NAME/KEY: Amidation
<222> LOCATION: (1)
<223> OTHER INFORMATION: Xaa stands for Acetylation
<220> FEATURE:
<221> NAME/KEY: Amidation
<222> LOCATION: (15)
<223> OTHER INFORMATION: Xaa stands for Aib

<400> SEQUENCE: 19

Xaa Leu Ser Thr Ala Val Leu Gly Lys Leu Ser Gln Glu Leu Xaa
1               5                   10                  15

Lys Leu Gln Thr Tyr Pro Arg Thr Asn Thr Gly Ser Gly Thr Pro
                20                  25                  30

<210> SEQ ID NO 20
<211> LENGTH: 29
<212> TYPE: PRT
<213> ORGANISM: Artificial Sequence
<220> FEATURE:
<223> OTHER INFORMATION: Salmon Calcitonin
<220> FEATURE:
<221> NAME/KEY: Amidation
<222> LOCATION: (1)
<223> OTHER INFORMATION: Xaa stands for Isocaproyl

<400> SEQUENCE: 20

Xaa Ser Thr Ala Val Leu Gly Lys Leu Ser Gln Glu Leu His Lys
1               5                   10                  15

Leu Gln Thr Tyr Pro Arg Thr Asn Thr Gly Ser Gly Thr Pro
                20                  25

<210> SEQ ID NO 21
```

```
<211> LENGTH: 30
<212> TYPE: PRT
<213> ORGANISM: Artificial Sequence
<220> FEATURE:
<223> OTHER INFORMATION: Salmon Calcitonin
<220> FEATURE:
<221> NAME/KEY: Amidation
<222> LOCATION: (1)
<223> OTHER INFORMATION: Xaa stands for a or c or t/u

<400> SEQUENCE: 21

Xaa Leu Ser Thr Ala Val Leu Gly Lys Leu Ser Gln Glu Leu His
 1               5                  10                  15

Lys Leu Gln Thr Tyr Pro Arg Thr Asn Thr Gly Ser Gly Thr Pro
            20                  25                  30

<210> SEQ ID NO 22
<211> LENGTH: 29
<212> TYPE: PRT
<213> ORGANISM: Artificial Sequence
<220> FEATURE:
<223> OTHER INFORMATION: Salmon Calcitonin
<220> FEATURE:
<221> NAME/KEY: Amidation
<222> LOCATION: (1)
<223> OTHER INFORMATION: Xaa stands for Adamantacetyl

<400> SEQUENCE: 22

Xaa Ser Thr Ala Val Leu Gly Lys Leu Ser Gln Glu Leu His Lys
 1               5                  10                  15

Leu Gln Thr Tyr Pro Arg Thr Asn Thr Gly Ser Gly Thr Pro
            20                  25

<210> SEQ ID NO 23
<211> LENGTH: 29
<212> TYPE: PRT
<213> ORGANISM: Artificial Sequence
<220> FEATURE:
<223> OTHER INFORMATION: Salmon Calcitonin
<220> FEATURE:
<221> NAME/KEY: Amidation
<222> LOCATION: (1)
<223> OTHER INFORMATION: Xaa stands for CH3CO

<400> SEQUENCE: 23

Xaa Ser Thr Ala Val Leu Gly Lys Leu Ser Gln Glu Leu His Lys
 1               5                  10                  15

Leu Gln Thr Tyr Pro Arg Thr Asn Thr Gly Ser Gly Thr Pro
            20                  25

<210> SEQ ID NO 24
<211> LENGTH: 29
<212> TYPE: PRT
<213> ORGANISM: Artificial Sequence
<220> FEATURE:
<223> OTHER INFORMATION: Salmon Calcitonin
<220> FEATURE:
<221> NAME/KEY: Amidation
<222> LOCATION: (1)
<223> OTHER INFORMATION: Xaa stands for Cyclohexylpropionyl

<400> SEQUENCE: 24

Xaa Ser Thr Ala Val Leu Gly Lys Leu Ser Gln Glu Leu His Lys
 1               5                  10                  15

Leu Gln Thr Tyr Pro Arg Thr Asn Thr Gly Ser Gly Thr Pro
            20                  25
```

```
<210> SEQ ID NO 25
<211> LENGTH: 29
<212> TYPE: PRT
<213> ORGANISM: Artificial Sequence
<220> FEATURE:
<223> OTHER INFORMATION: Salmon Calcitonin
<220> FEATURE:
<221> NAME/KEY: Amidation
<222> LOCATION: (1)
<223> OTHER INFORMATION: Xaa stands for Cyclopentyl C (0)

<400> SEQUENCE: 25

Xaa Ser Thr Ala Val Leu Gly Lys Leu Ser Gln Glu Leu His Lys
 1               5                  10                  15

Leu Gln Thr Tyr Pro Arg Thr Asn Thr Gly Ser Gly Thr Pro
                20                  25

<210> SEQ ID NO 26
<211> LENGTH: 29
<212> TYPE: PRT
<213> ORGANISM: Artificial Sequence
<220> FEATURE:
<223> OTHER INFORMATION: Salmon Calcitonin
<220> FEATURE:
<221> NAME/KEY: Amidation
<222> LOCATION: (1)
<223> OTHER INFORMATION: Xaa stands for Decanoyl

<400> SEQUENCE: 26

Xaa Ser Thr Ala Val Leu Gly Lys Leu Ser Gln Glu Leu His Lys
 1               5                  10                  15

Leu Gln Thr Tyr Pro Arg Thr Asn Thr Gly Ser Gly Thr Pro
                20                  25

<210> SEQ ID NO 27
<211> LENGTH: 19
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (1)
<223> OTHER INFORMATION: Xaa stands for Leu-Leu, Val-Leu, Ile-Leu,
      tert-Leu-Leu, Nle-Neu, and Ala-Thr, and N-acylated
<220> FEATURE:
<221> NAME/KEY: Amidation
<222> LOCATION: (2)
<223> OTHER INFORMATION: Xaa stands for Gly, Glu, Asn or Aib
<220> FEATURE:
<221> NAME/KEY: Amidation
<222> LOCATION: (3)
<223> OTHER INFORMATION: Xaa stands for Arg, Orn, Lys and amidated
      derivatives
<220> FEATURE:
<221> NAME/KEY: Amidation
<222> LOCATION: (5)
<223> OTHER INFORMATION: Xaa stands for Ser-Gln, Thr-Gln, Ala-Asn and
      Thr-Asn
<220> FEATURE:
<221> NAME/KEY: Amidation
<222> LOCATION: (8)
<223> OTHER INFORMATION: Xaa stands for His, Aib, Ile, Leu and Val
<220> FEATURE:
<221> NAME/KEY: Amidation
<222> LOCATION: (9)
<223> OTHER INFORMATION: Xaa stands for Arg, Orn, Lys and amidated
      derivatives
<220> FEATURE:
<221> NAME/KEY: Amidation
<222> LOCATION: (18)
<223> OTHER INFORMATION: Xaa stands for Thr-Gly-Ser-Asn-Thr-Tyr-NH2,
      Thr-Gly-Ser-Gly-Thr-Pro-NH2,
```

```
        Val-Gly-Ser-Asn-Thr-Tyr-NH2,
        Val-Gly-Ser-Gly-Thr-Pro-NH2
<220> FEATURE:
<221> NAME/KEY: Amidation
<222> LOCATION: (19)
<223> OTHER INFORMATION: Xaa stands for Z3  is OH or NH2

<400> SEQUENCE: 27

Xaa Xaa Xaa Leu Xaa Glu Leu Xaa Xaa Leu Gln Thr Tyr Pro Arg
  1               5                  10                  15

Thr Asn Xaa Xaa

<210> SEQ ID NO 28
<211> LENGTH: 6
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (1)
<223> OTHER INFORMATION: Xaa stands for Leu, Val, Ile, tert-Leu, Nva,
      Abu, and Nle or N-acylated derivatives
<220> FEATURE:
<221> NAME/KEY: Amidation
<222> LOCATION: (4)
<223> OTHER INFORMATION: Xaa stands for Ala, Ser, Cys and Thr

<400> SEQUENCE: 28

Xaa Ser Thr Xaa Val Leu
  1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (7)
<223> OTHER INFORMATION: Xaa stands for NH2

<400> SEQUENCE: 29

Thr Gly Ser Asn Thr Tyr Xaa
  1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (7)
<223> OTHER INFORMATION: Xaa stands for NH2

<400> SEQUENCE: 30

Thr Gly Ser Gly Thr Pro Xaa
  1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
```

```
<222> LOCATION: (7)
<223> OTHER INFORMATION: Xaa stands for NH2

<400> SEQUENCE: 31

Val Gly Ser Asn Thr Tyr Xaa
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptides
<220> FEATURE:
<221> NAME/KEY: Amidation
<222> LOCATION: (7)
<223> OTHER INFORMATION: Xaa stands for NH2

<400> SEQUENCE: 32

Val Gly Ser Gly Thr Pro Xaa
1               5
```

MIXED AMYLIN ACTIVITY COMPOUNDS

RELATED APPLICATIONS

This application is a National Stage application of International Application No. PCT/US99/02603, filed Feb. 5, 1999, which claims the benefit under 35 U.S.C. §119 of U.S. Provisional Application No. 60/074,746, filed Feb. 13, 1998.

INCORPORATION OF SEQUENCE LISTING

A paper copy of the Sequence Listing and a computer readable form of the sequence listing on diskette, containing the file named 18528038.txt, which is 17095 bytes in size (measured in Windows XP), and which was created on Apr. 18, 2005, are herein incorporated by reference.

FIELD OF THE INVENTION

The present invention is directed to compounds which inhibit certain activities of amylin but which also act as amylin agonists with respect to other amylin activities. These compounds are useful in treating disturbances in fuel metabolism in mammals, including, but not limited to diabetes mellitus, including Type I diabetes and Type II diabetes, impaired glucose tolerance, insulin resistance and Syndrome X.

BACKGROUND AND INTRODUCTION TO THE INVENTION

Diabetes mellitus is a serious metabolic disease that is defined by the presence of chronically elevated levels of blood glucose (hyperglycemia). This state of hyperglycemia is the result of a relative or absolute lack of activity of the peptide hormone, insulin. Insulin is produced and secreted by the β cells of the pancreas. Insulin is reported to promote glucose utilization, protein synthesis, and the formation and storage of carbohydrate energy as glycogen. Glucose is stored in the body as glycogen, a form of polymerized glucose, which may be converted back into glucose to meet metabolism requirements. Under normal conditions, insulin is secreted at both a basal rate and at enhanced rates following glucose stimulation, all to maintain metabolic homeostasis by the conversion of glucose into glycogen.

The term diabetes mellitus encompasses several different hyperglycemic states. These states include Type I (insulin-dependent diabetes mellitus or IDDM) and Type II (non-insulin dependent diabetes mellitus or NIDDM) diabetes. The hyperglycemia present in individuals with Type I diabetes is associated with deficient, reduced, or nonexistent levels of insulin which are insufficient to maintain blood glucose levels within the physiological range. Treatment of Type I diabetes involves administration of replacement doses of insulin, generally by a parenteral route. The hyperglycemia present in individuals with Type II diabetes is initially associated with normal or elevated levels of insulin; however, these individuals are unable to maintain metabolic homeostasis due to a state of insulin resistance in peripheral tissues and liver and, as the disease advances, due to a progressive deterioration of the pancreatic β cells which are responsible for the secretion of insulin. Thus, initial therapy of Type II diabetes may be based on diet and lifestyle changes augmented by therapy with oral hypoglycemic agents such as sulfonylureas. Insulin therapy is often required, however, especially in the latter states of the disease, in attempting to produce some control of hyperglycemia and minimize complications of the disease.

The structure and biology of amylin have previously been reviewed. See, for example, Young, *Current Opinion in Endocrinology and Diabetes,* 4:282–290 (1997); Gaeta and Rink, *Med. Chem. Res.,* 3:483–490 (1994); and, Pittner et al., *J. Cell. Biochem.,* 55S:19–28 (1994). Amylin is a 37 amino acid peptide hormone. It was isolated, purified and chemically characterized as the major component of amyloid deposits in the islets of pancreases of deceased human Type II diabetics (Cooper et al., *Proc. Natl. Acad. Sci. USA,* 84:8628–8632 (1987)). The amylin molecule has two important post-translational modifications: the C-terminus is amidated, i.e., the 37th residue is tyrosinamide, and the cysteines in positions 2 and 7 are cross-linked to form an intra-molecular N-terminal loop, both of which are essential for full biologic activity (Cooper et al., *Proc. Natl. Acad. Sci. USA,* 85:7763–7766 (1988)). Amylin is the subject of U.S. Pat. No. 5,367,052, issued Nov. 22, 1994.

In Type I diabetes and late stage Type II diabetes, amylin has been shown to be deficient and combined replacement with insulin has been proposed as a preferred treatment over insulin alone in all forms of insulin-dependent diabetes. The use of amylin and amylin agonists for the treatment of diabetes mellitus is the subject of U.S. Pat. No. 5,175,145, issued Dec. 29, 1992. Pharmaceutical compositions containing amylin and amylin plus insulin are described in U.S. Pat. No. 5,124,314, issued Jun. 23, 1992.

Excess amylin action has been said to mimic key features of the earlier stages of Type II diabetes and amylin blockade has been proposed as a novel therapeutic strategy. It has been disclosed in U.S. Pat. No. 5,266,561, issued Nov. 30, 1993, that amylin causes reduction in both basal and insulin-stimulated incorporation of labeled glucose into glycogen in skeletal muscle. The latter effect was also disclosed to be shared by calcitonin gene related peptide (CGRP) (see also Leighton and Cooper, *Nature,* 335:632–635 (1988)). Amylin and CGRP were approximately equipotent, showing marked activity at 1 to 10 nM. Amylin is also reported to reduce insulin-stimulated uptake of glucose into skeletal muscle and reduce glycogen content (Young et al., *Amer. J. Physiol.,* 259:45746–1 (1990)). The treatment of Type II diabetes and insulin resistance with amylin antagonists is disclosed.

Amylin is primarily synthesized in pancreatic beta cells and is secreted in response to nutrient stimuli such as glucose and arginine. Studies with cloned beta-cell tumor lines (Moore et al., *Biochem. Biophys. Res. Commun.,* 179(1) (1991)) and perfused rat pancreases (Ogawa et al., *J. Clin. Invest.,* 85:973–976 (1990)) have shown that short pulses, 10 to 20 minutes, of nutrient secretagogues such as glucose and arginine, stimulate release of amylin as well as insulin. The molar amylin:insulin ratio of the secreted proteins varies between preparations from about 0.01 to 0.4, but appears not to vary much with acute stimuli in any one preparation. However, during prolonged stimulation by elevated glucose, the amylin:insulin ratio can progressively increase (Gedulin et al., *Biochem. Biophys. Res. Commun.,* 180(1):782–789 (1991)). Thus, amylin and insulin are not always secreted in a constant ratio.

It has been discovered and reported that certain actions of amylin are similar to non-metabolic actions of CGRP and calcitonin; however, the metabolic actions of amylin discovered during investigations of this recently identified protein appear to reflect its primary biologic role. At least some of these metabolic actions are mimicked by CGRP, albeit at doses which are markedly vasodilatory (see, e.g., Leighton and Cooper, *Nature,* 335:632–635 (1988)); Molina et al., *Diabetes,* 39:260–265 (1990)).

The first discovered action of amylin was the reduction of insulin-stimulated incorporation of glucose into glycogen in rat skeletal muscle (Leighton and Cooper, *Nature*, 335:632–635 (1988)); the muscle, thus, became "insulin-resistant". Subsequent work with rat soleus muscle ex-vivo and in vitro has indicated that amylin reduces glycogen synthase activity, promotes conversion of glycogen phosphorylase from the inactive b form to the active a form, promotes net loss of glycogen (in the presence or absence of insulin), increases glucose-6-phosphate levels, and can increase lactate output (see, e.g., International Patent Application No. PCT/US92/00185, published Jul. 23, 1992 (international Publication No. WO 92/11863). Amylin appears not to affect glucose transport per se (e.g., Pittner et al., *FEBS Letts.*, 365(1):98–100 (1995)). Studies of amylin and insulin dose-response relations show that amylin acts as a noncompetitive or functional antagonist of insulin in skeletal muscle (Young et al., *Am. J. Physiol.*, 263(2):E274–E281 (1992)). There is no evidence that amylin interferes with insulin binding to its receptors, or the subsequent activation of insulin receptor tyrosine kinase (Follett et at., *Clinical Research*, 39(1) :39A (1991)); Koopmans et al., *Diabetologia*, 34:218–224 (1991)).

It is believed that amylin acts through receptors present in plasma membranes. Studies of amylin and CGRP, and the effect of selective antagonists, have led to reports that amylin acts via its own receptor (Beaumont et al., *Br. J. Pharmacol.*, 115(5):713–715 (1995); Wang et al., *FEBS Letts.*, 219:195–198 (1991 b)), in contrast to the conclusion of other workers that amylin may act primarily at CGRP receptors (e.g., Chantry et al., *Biochem. J.*, 277:139–143 (1991)); Zhu et al., *Biochem. Biophys. Res. Commun.*, 177(2):771–776 (1991)). Amylin receptors and their use in methods for screening and assaying for amylin agonist and antagonist compounds are described in U.S. Pat. No. 5,264,372, issued Nov. 23, 1993.

While amylin has marked effects on hepatic fuel metabolism in vivo, there is no general agreement as to what amylin actions are seen in isolated hepatocytes or perfused liver. The available data do not support the idea that amylin promotes hepatic glycogenolysis, i.e., it does not act like glucagon (e.g., Stephens et al., *Diabetes*, 40:395–400 (1991); Gomez-Foix et al., *Biochem J.*, 276:607–610 (1991)). It has been suggested that amylin may act on the liver to promote conversion of lactate to glycogen and to enhance the amount of glucose able to be liberated by glucagon. In this way, amylin could act as an anabolic partner to insulin in liver, in contrast to its catabolic action in muscle.

In fat cells, contrary to its action in muscle, amylin has no detectable actions on insulin-stimulated glucose uptake, incorporation of glucose into triglyceride, $CO_2$ production (Cooper et al., *Proc. Natl. Acad. Sci.*, 85:7763–7766 (1988)) epinephrine-stimulated lipolysis, or insulin-inhibition of lipolysis (Lupien and Young, "Diabetes Nutrition and Metabolism—Clinical and Experimental," Vol. 6(1), pages 1318 (February 1993)). Amylin thus exerts tissue-specific effects, with direct action on skeletal muscle, marked indirect (via supply of substrate) and perhaps direct effects on liver, while adipocytes appear "blind" to the presence or absence of amylin.

It has also been reported that amylin can have marked effects on secretion of insulin. In the perfused pancreas (Silvestre et al., *Reg. Pept.*, 31:23–31 (1990)), and in the intact rat (Young et at., *Mol. Cell. Endocrinol.*, 84:R1–R5 (1992)), some experiments indicate that amylin inhibits insulin secretion. Other workers, however, have been unable to detect effects of amylin on isolated β-cells, on isolated islets, or in the whole animal (see Broderick et al., *Biochem. Biophys. Res. Commun.*, 177:932–938 (1991) and references therein).

Amylin and amylin agonists have also been shown to suppress glucagon secretion. When influences that would otherwise affect glucagon secretion were controlled (plasma glucose, insulin and blood pressure), amylin reportedly suppressed the glucagon response to arginine in rats. Gedulin et al., *Metabolism*, 46:67–70 (1997). The amylin anaogue, pramlintide, has been reported to eliminate the post-prandial surge in glucagon concentration in subjects wth Type I diabetes. Fineman et al., *Diabetes*, 40:30A (1997). Pramlintide, and other amylin agonist analogues, are described and claimed in U.S. Pat. No. 5,686,411, issued Nov. 11, 1997. A glucagonostatic effect of amylin has not been demonstrated in the isolated perfused pancreas (Silvestre et al., *Regul. Pept.*, 31:23–31 (1990), indicating that amylin may exert its glucagonostatic action via an extrapancreatic mechanism. The observation that suppression of glucagon secretion does not occur with the amylin analogue, pramlintide, in humans during insulin-induced hypoglycemia (Nyholm et al., *J. Clin. Endocrin. Metab.*, 81:1083–1089 (1996); Kolterman et al., *Diabetologia*, 39:492–499 (1996)) further supports the idea that this effect is not directly on a cells but could be centrally mediated.

Amylin and amylin agonists potently inhibit gastric emptying in rats (Young et al., *Diabetologia* 38(6):642–648 (1995)), dogs (Brown et al., *Diabetes* 43(Suppl 1):172A (1994)) and humans (Macdonald et al., *Diabetologia* 38(Suppl 1):A32 (abstract 118) (1995)). Gastric emptying is reportedly accelerated in amylin-deficient Type I diabetic BB rats (Young et al., *Diabetologia*, supra; Nowak et al., *J. Lab. Clin. Med.*, 123(1):110–6 (1994)) and in rats treated with the amylin antagonist, AC187 (Gedulin et al., *Diabetologia*, 38(Suppl 1):A244 (1995). The effect of amylin on gastric emptying appears to be physiological (operative at concentrations that normally circulate).

Non-metabolic actions of amylin include vasodilator effects which may be mediated by interaction with CGRP vascular receptors. Reported in vivo tests suggest that amylin is at least about 100 to 1000 times less potent than CGRP as a vasodilator (Brain et al., *Eur. J. Pharmacol.*, 183:2221 (1990); Wang et al., *FEBS Letts.*, 291:195–198 (1991)).

Injected into the brain, or administered peripherally, amylin has been reported to suppress food intake, e.g., Chance et al., *Brain Res.*, 539:352–354 (1991)), an action shared with CGRP and calcitonin. The effective concentrations at the cells that mediate this action are not known. Amylin has also been reported to have effects both on isolated osteoclasts where it caused cell quiescence, and in vivo where it was reported to lower plasma calcium by up to 20% in rats, in rabbits, and in humans with Paget's disease (see, e.g., Zaidi et al., *Trends in Endocrinal. and Metab.*, 4:255–259 (1993). From the available data, amylin seems to be 10 to 30 times less potent than human calcitonin for these actions. Interestingly, it was reported that amylin appeared to increase osteoclast cAMP production but not to increase cytosolic $Ca^{2+}$, while calcitonin does both (Alam et al., *Biochem. Biophys. Res. Commun.*, 179(1):134–139 (1991)). It was suggested, though not established, that amylin may act via a single receptor type whereas calcitonin may act via two receptors, one of which is common to amylin activity.

It has also been discovered that, surprisingly in view of its previously described renal vasodilator and other properties, amylin markedly increases plasma renin activity in intact rats when given subcutaneously in a manner that avoids any disturbance of blood pressure. This latter point is important because lowered blood pressure is a strong stimulus to renin release. Amylin antagonists, such as amylin receptor antagonists, including those selective for amylin receptors compared to CGRP and/or calcitonin receptors, can be used to block the amylin-evoked rise of plasma renin activity. The use of amylin antagonists to treat renin-related disorders is described in U.S. Pat. No. 5,376,638, issued Dec. 27, 1994.

In normal humans, fasting amylin levels from 1 to 10 pM and post-prandial or post-glucose levels of 5 to 20 pM have been reported (see, e.g., Koda et al., *The Lancet*, 339:1179–1180 (1992)). In obese, insulin-resistant individuals, post-food amylin levels can go higher, reaching up to about 50 pM. For comparison, the values for fasting and post-prandial insulin are 20 to 50 pM, and 100 to 300 pM respectively in healthy people, with perhaps 3- to 4-fold higher levels in insulin-resistant people. In Type I diabetes, where beta cells are destroyed, amylin levels are at or below the levels of detection and do not rise in response to glucose (Koda et al., *The Lancet*, 339:1179–1180 (1992)). In normal mice and rats, basal amylin levels have been reported from 30 to 100 pM, while values up to 600 pM have been measured in certain insulin-resistant, diabetic strains of rodents (e.g., Huang et al., *Hypertension*, 19:I-101–I-109 (1991)).

In mammals, calcitonin functions in the regulation of bone marrow turnover and calcium metabolism. Calcitonin, which is caused to be released from the thyroid by elevated serum calcium levels, produces actions on bone and other organs which tend to reduce serum calcium levels. Calcitonin inhibits osteoclast activity and reduces bone resorption, thereby reducing serum calcium levels. Calcitonin also alters calcium, phosphate and electrolyte excretion by the kidney, although the physiological significance of this is not reported. Calcitonin has been used clinically for treatment of disorders of calcium metabolism and pain, and its relationship to increased glucose levels in mammals has been the subject of varying reports. See, e.g., Azria et al., "Calcitonins—Physiological and Pharmacological Aspects," pp. 24–25 (Springer-Verlag 1989). The use of calcitonins in the treatment of diabetes mellitus is described in U.S. Pat. No. 5,321,008 issued Jun. 14, 1994 and U.S. Pat. No. 5,508,260 issued Apr. 16, 1996.

Certain compounds reported to be calcitonin derivatives have been said to lower the calcium plasma level and to influence bone metabolism (U.S. Pat. No. 4,758,550 to Cardinaux et al.).

SUMMARY OF THE INVENTION

The present invention provides novel compounds having activity in regulating the metabolic effects mediated by amylin in mammals. Surprisingly, these compounds inhibit certain effects of amylin and also act as amylin agonists for other of amylin's effects.

Among other factors, the present invention is based on our unexpected findings that the compounds of the present invention exhibit a biological profile of mixed amylin antagonism and agonism coupled with relatively weak binding at CGRP receptors. In particular, these compounds have been determined to act as amylin antagonists in blocking the glycogen-related responses associated with amylin action in muscle and also to act as amylin agonists in inhibiting of gastric emptying. It is believed that due to this surprising combination of biological effects, these compounds will be useful in treating diabetes, indicating Type I diabetes, due to their effects on inhibition of gastric emptying, and will also be useful in treating impaired glucose tolerance, insulin resistance, Type II diabetes, particularly early Type II diabetes, and Syndrome X due to their effects on glucose metabolism. Additionally, due to their action on plasma calcium levels, the present compounds may be particularly advantageous.

The compounds of the present invention are also useful in performing studies relating to receptor characterization, for example, characterization of receptors at which amylins bind. Additionally, the present compounds are useful as test compounds and control samples in the assays described in the Examples below.

According to the present invention, provided are compounds of the formula:

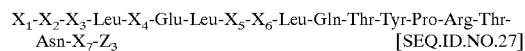
$X_1$-$X_2$-$X_3$-Leu-$X_4$-Glu-Leu-$X_5$-$X_6$-Leu-Gln-Thr-Tyr-Pro-Arg-Thr-Asn-$X_7$-$Z_3$     [SEQ.ID.NO.27]

wherein (a) $X_1$ is (i) a group having two amino acid residues selected from the group consisting of Leu-Leu, Val-Leu, Ile-Leu, tert-Leu-Leu, Nle-Leu, and Ala-Thr, and N-acylated derivatives thereof; or is (ii) the group $Z_1$-Ser-Thr-$Z_2$-Val-Leu [SEQ.ID.NO. 28] wherein $Z_1$ is an amino acid residue selected from the group consisting of Leu, Val, Ile, tert-Leu, Nva, Abu, and Nle or an N-acylated derivative thereof or $Z_1$ is an alkanoyl group; and $Z_2$ is an amino acid residue selected from the group consisting of Ala, Ser, Cys, and Thr;

(b) $X_2$ is an amino acid residue selected from the group consisting of Gly, Glu, Asn or Aib;

(c) $X_3$ is an amino acid residue selected from the group consisting of Arg, Orn, Lys and ε-amidated derivatives thereof;

(d) $X_4$ is a group having two amino acid residues selected from the group consisting of Ser-Gln, Thr-Gln, Ala-Asn and Thr-Asn;

(e) $X_5$ is an amino acid residue selected from the group consisting of His, Aib, Ile, Leu and Val;

(f) $X_6$ is an amino acid residue selected from the group consisting of Arg, Orn and Lys and ε-amidated derivatives thereof;

(g) $X_7$ is a group having six amino acid residues selected from the group consisting of
  (i) Thr-Gly-Ser-Asn-Thr-Tyr-$NH_2$ [SEQ.ID.NO. 29];
  (ii) Thr-Gly-Ser-Gly-Thr-Pro-$NH_2$ [SEQ.ID.NO. 30];
  (iii) Val-Gly-Ser-Asn-Thr-Tyr-$NH_2$ [SEQ.ID.NO. 31];
  (iv) Val-Gly-Ser-Gly-Thr-Pro-$NH_2$ [SEQ.ID.NO. 32]; and (h) $Z_3$ is OH or $NH_2$;

with the proviso that the compound does not have the formula of any of SEQ. ID. Nos. 14 to 26;
and pharmaceutically acceptable salts thereof.

Definitions

In accordance with the present invention and as used herein, the following terms are defined to have the following meanings, unless explicitly stated otherwise.

The term "amylin" is understood to include the human peptide hormone amylin secreted from the beta cells of the pancreas.

"Amylin agonist" is also a term known in the art, and refers to a compound which has biological activities of amylin. An amylin agonist may be a peptide or a non-peptide compound. Such compounds may act as amylin agonists, normally, it is presently believed, by virtue of binding to or otherwise directly or indirectly interacting with an amylin receptor or other receptor or receptors with which amylin itself may interact to elicit a biological response.

The term "amylin antagonist" refers to a compound which inhibits effects of amylin. An amylin antagonist may be a peptide or a non-peptide compound.

The term "alkanoyl" refers to the group RC(=O)— wherein R is a straight chain or branched chain alkyl group, which may be derived from a corresponding carboxylic acid.

The term "amino acid" refers to natural amino acids, unnatural amino acids, and amino acid analogs, all in their D and L stereoisomers if their structure allow such stereoisoreric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), typtophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid (Abu), 4-aminobutyric acid, 6-aminocaproic acid, 2-aminoheptanoic acid, 2-aminoisobutyric acid (Aib), 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline (Nva), norleucine (Nle), ornithine (Orn), pentylglycine, pipecolic acid and thioproline. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically codified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is an amino acid side chain, typically H or a carbon containing substitutent; or (2)

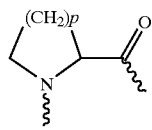

wherein p is 1, 2 or 3 representing the azetidinecarboxylic acid, proline or pipecolic acid residues, respectively.

The term "lower" referred to herein in connection with organic radicals such as alkyl groups defines such groups with up to and including about 6, preferably up to and including 4 and advantageously one or two carbon atoms. Such groups may be straight chain or branched chain.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

In addition, the following abbreviations stand for the following:

"Ac" refers to acetyl.
"ACN" or "CH$_3$CN" refers to acetonitrile.
"Boc", "tBoc" or "Tboc" refers to t-butoxy carbonyl.
"DCC" refers to N,N'-dicyclohexylcarbodiimide.
"Fmoc" refers to fluorenylmethoxycarbonyl.
"For" refers to formamidated, for example, "Lys(For)" refers to formamidated lysine.
"HBTU" refers to 2-(1H-benzotriazol-1-yl)-1,1,3,3,-tetramethyluronium hexaflurophosphate.
"HOBt" refers to 1-hydroxybenzotriazole monohydrate.

BRIEF DESCRIPTION OF THE DRAWINGS

FIG. 8 depicts the amino acid sequences of Compounds 1 to 13 [SEQ.ID.NOS. 1 to 13].

FIG. 9 depicts the amino acid sequences of certain peptide compounds reported in the literature [SEQ.ID.NOS. 14 to 26]. The references for the sequences are as follows: SEQ.ID.NO. 14: 4–32 salmon calcitonin; SEQ.ID.NO. 15: 8–32 salmon calcitonin; SEQ.ID.NOS. 16 and 17: U.S. Pat. No. 5,580,953; SEQ.ID.NOS. 18 and 19: Gamse et al., J. Bone Min. Res. 8 (Suppl 1); S200, Abstract #334 (1993); and SEQ.ID.NOS. 20 to 26: U.S. Pat. No. 4,758,550.

DETAILED DESCRIPTION OF THE INVENTION

Preferred Compounds

Figure 1:
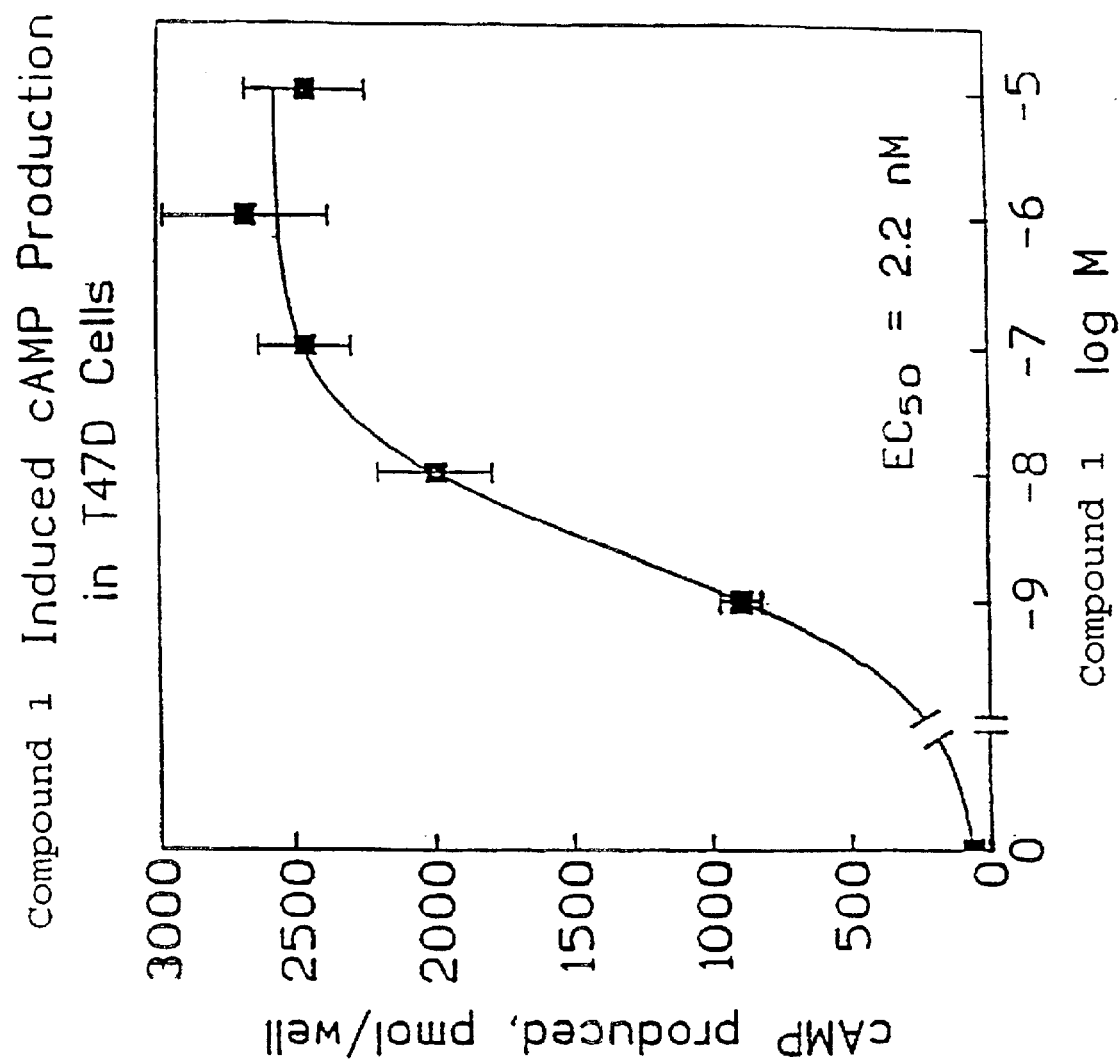
FIG. 1 depicts calcitonin receptor-coupled stimulation of adenyl cyclase by the compound of Example 1 ("Compound 1") [SEQ.ID.NO. 1]. Cyclic AMP accumulation in T47D cells was measured as a function of test compound concentration.

According to the present invention, provided are compounds of formula:

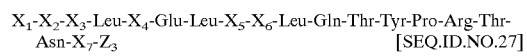

wherein
(a) X$_1$ is (i) a group having two amino acid residues selected from the group consisting of Leu-Leu, Val-Leu, Ile-Leu, tert-Leu-Leu, Nle-Leu, and Ala-Thr, and N-acylated derivatives thereof; or (ii) the group $Z_1$-Ser-Thr-$Z_2$-Val-Leu [SEQ.ID.NO.28] wherein $Z_1$ is an amino acid residue selected from the group consisting of Leu, Val, Ile, tert-Leu, Nva, Abu, and Nle or N-acylated derivatives thereof or $Z_1$ is an alkanyl group; and $Z_2$ is a amino acid residue selected from the group consisting of Ala, Ser, Cys, and Thr;

(b) $X_2$ is an amino acid residue selected from the group consisting of Gly, Glu, Asn and Aib;

(c) $X_3$ is an amino acid residue selected from the group consisting of Arg, Orn, Lys and ε-amidated derivatives thereof;

(d) $X_4$ is a group having two amino acid residues selected from the group consisting of Ser-Gln, Thr-Gln, Ala-Asn and Thr-Asn;

(e) $X_5$ is an amino acid residue selected from the group consisting of His, Aib, Ile, Leu and Val;

(f) $X_6$ is an amino acid residue selected from the group consisting of Arg, Orn and Lys and ε-amidated derivatives thereof; and (g) $X_7$ is a group having 6 amino acid residues selected from the group consisting of
 (i) Thr-Gly-Ser-Asn-Thr-Tyr-$NH_2$ [SEQ.ID.NO. 29];
 (ii) Thr-Gly-Ser-Gly-Thr-Pro-$NH_2$ [SEQ.ID.NO. 30];
 (iii) Val-Gly-Ser-Asn-Thr-Tyr-$NH_2$ [SEQ.ID.NO. 31];
 (iv) Val-Gly-Ser-Gly-Thr-Pro-$NH_2$ [SEQ.ID.NO. 32]; and (h) $Z_3$ is OH or $NH_2$ with the proviso that the compound does not have the formula of any of SEQ. ID. NOS. 14 to 26. Also included within the scope of the present invention are pharmaceutically acceptable salts of these compounds.

Preferred $X_1$ groups include $Z_1$-Ser-Thr-$Z_2$-Val-Leu. Preferably $Z_1$ is an alkanoyl group to give an N-terminal amidation derivative of serine with a carboxylic acid or Leu. Suitable carboxylic acids include straight chain or branched chain carboxylic acids of 1 to about 10 carbon atoms, more preferably of about 6 to about 8 carbon atoms. More preferably $Z_1$ is an alkanoyl group to give an N-terminal amidation. Especially preferred $Z_1$ groups include 4-methylpentanoyl. Preferred $Z_2$ groups include Ala or Cys, more preferably Ala.

Preferred $X_2$ groups include Gly.

Preferred $X_3$ groups include ε-amidated derivatives which are amidated with a carboxylic acid having 1 to 8 carbon atoms. Preferably $X_3$ is Lys ε-amidated with formic or acetic acid. Especially preferred $X_3$ groups include Lys(For).

Preferred $X_4$ groups include Ser-Glu.

Preferred $X_5$ groups include His or Aib. More preferably $X_5$ is Aib.

Preferred $X_6$ groups include ε-amidated derivatives which are amidated with a carboxylic acid having 1 to 8 carbon atoms. Preferably $X_3$ is Lys ε-amidated with formic or acetic acid. Especially preferred $X_3$ groups include Lys(For).

Preferred $X_7$ groups include Thr-Gly-Ser-Asn-Thr-Tyr-$NH_2$ [SEQ.ID.NO. 29] and Thr-Gly-Ser-Gly-Thr-Pro-$NH_2$ [SEQ.ID.NO. 30].

Preferably $Z_3$ is $NH_2$.

According to an especially preferred aspect provided are compounds wherein $X_2$ is Gly, $X_5$ is His or Aib, $X_4$ is Ser-Glu, $X_7$ is Thr-Gly-Ser-Asn-Thr-Tyr-$NH_2$ [SEQ.ID.NO. 29] or Thr-Gly-Ser-Gly-Thr-Pro-$NH_2$ [SEQ.ID.NO. 30], $X_1$ is $Z_1$ Ser-Thr-$Z_2$-Val-Leu, where preferably $Z_1$ is Leu or an alkanoyl group to give N-terminal amidation of serine with a carboxylic acid and $Z_2$ is Ala or Cys; $X_3$ and $X_6$ are ε-amidated with a carboxylic acid. For $Z_1$, preferred are carboxylic acids having 1 to about 10 carbon atoms, more preferably about 6 to about 8 carbon atoms. Especially preferred carboxylic acids include 4-methylpentanoic acid. More preferably $Z_1$ is an alkanoyl group to give an N-terminal amidation. More preferably $X_3$ and $X_6$ are Lys amidated with formic or acetic acid. Especially preferred $X_3$ and $X_6$ groups include Lys(For).

Preferred peptide compounds of the present invention include those having amino acid sequences of SEQ.ID.NOS. 1 to 13 ("Compounds 1 to 13," respectively). Especially preferred peptide compounds include Compounds 1 and 2.

Amylin-Related Activity

Activities of the compounds of the present invention can be confirmed and quantified by performing various screening assays, including the receptor binding assays described below in Example A, the adenyl cyclase stimulation assay described below in Example B, the soleus muscle assay described below in Example C, the measurement of plasma glucose, lactate and calcium levels as described below in Examples D and E, and the gastric emptying assay described below in Example F.

The nucleus accumbens receptor binding assay, a competition assay which measures the ability of compounds to bind specifically to membrane-bound amylin receptors, is described in U.S. Pat. No. 5,264,372, issued Nov. 23, 1993, the disclosure of which is incorporated herein by reference. The nucleus accumbens receptor binding assay is also described in Example A below. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et al. (ALLFIT, Version 2.7 (NIH, Bethesda, Md. 20892)). Munson and Rodbard, *Anal. Biochem.* 107:220–239 (1980).

The SK-N-MC cell binding assay, which measures the ability of compounds to bind specifically to CGRP receptors, is described in Example A below. The preferred source of the membrane preparations used in the assay are SK-N-MC human neuroblastoma cells which have been shown to contain a high-affinity CGRP receptor that is coupled to adenyl cyclase and which has binding and specificity characteristics similar to CGRP receptors present in several other tissues (VanValen et al., *Neuroscience Letters* 119:195–198, (1990).

The T47D cell binding assay which measures the ability of compounds to bind specifically to calcitonin receptors, is described in Example A below. Membranes are prepared from T47D breast carcinoma cell cultures. Binding to calcitonin receptors is quantified by displacement of labeled salmon calcitonin.

Functional activity of compounds at calcitonin receptors can be measured according to the adenyl cyclase assay described in Example B below. Human T47D and MCF7 breast carcinoma cells contain calcitonin receptors coupled to the stimulation of adenyl cyclase activity. In these cells, calcitonin stimulates increases in cyclic AMP accumulation.

Assays of biological activity of compounds in the soleus muscle may be performed using previously described methods (Leighton, B. and Cooper, *Nature*, 335:632–635 (1988); Cooper, et al., *Proc. Natl. Acad. Sci. USA* 85:7763–7766 (1988)), in which amylin agonist activity may be assessed by measuring the inhibition of insulin-stimulated glycogen synthesis. The soleus muscle assay is also described in Example C below.

Methods of measuring effects of compounds on plasma glucose, lactate and calcium levels are described in Examples D and E.

Methods of measuring the rate of gastric emptying are disclosed in, for example, Young et al., *Diabetologia*, 38(6):642–648 (1995). In a phenol red method, which is described in Example F below, conscious rats receive by gavage an a caloric gel containing methyl cellulose and a phenol red indicator. Twenty minutes after gavage, animals are anesthetized using halothane, the stomach exposed and clamped at the pyloric and lower esophageal sphincters, removed and opened into an alkaline solution. Stomach content may be derived from the intensity of the phenol red in the alkaline solution, measured by absorbance at a wavelength of 560 nm. In a tritiated glucose method, conscious rats are gavaged with tritiated glucose in water. The rats are gently restrained by the tail, the tip of which is anesthetized using lidocaine. Tritium in the plasma separated from tail blood is collected at various timepoints and detected in a beta counter. Test compounds are normally administered about one minute before gavage.

Preferably, compounds of the present invention exhibit activity in the nucleus accumbens receptor binding assay on the order of less than about 1 to 5 nM, and more preferably less than about 1 nM. In the soleus muscle assay these compounds preferably inhibit the effects of amylin in the concentration range of 1–100 nM, and more preferably in the range of 5–50 nM, and show $IC_{50}$ values on the order of less than about 1 to 2 $\mu$M. In the gastric emptying assays, preferred compounds show $ED_{50}$ values on the order of less than 100 $\mu$g/rat, and more preferably less than 10 $\mu$g/rat.

Preparation of Compounds

The compounds of the present invention may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein. A preferred resin for use with Fmoc chemistry which delivers a c-terminal amide is a Rink Amide MBRA resin (4-(2',2'-Dimethoxyphenyl-Fmoc-aminomethyl)-phenoxyacetamido-norleucyl-MBHA resin).

The solvents, amino acid derivatives and 4-methylbenzhydryl-amine resin used in the peptide synthesizer may be purchased from Applied Biosystems Inc. (Foster City, Calif.). Rink amide MBM resin is available from Novabiochem (La Jolla, Calif.). The following side-chain protected amino acids may be purchased from Applied Biosystems, Inc.: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys (Boc), Boc-Glu(Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Fmoc-Lys (For) and Fmoc-Aib may be purchased from Bachem, Inc. (Torrance, Calif.). Anisole, acetic anhydride, isocaproic acid, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt system and tBoc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6–12). Peptides may be also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10$\mu$, 2.2×25 cm; Vydac, Hesperia, Calif.) may be used to isolate peptides, and purity may be determined using a C4, C8 or C18 analytical column (5$\mu$, 0.46×25 cm; Vydac). Solvents (A=0.1% TFA/water and B=0.1% TFA/$CH_3CN$) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20–24 h). Hydrolysates may be derivatized and analyzed by standard methods (Cohen, et al., *The Pico Tag Method: A Manual of Advanced Techniques for Amino Acid Analysis*, pp. 11–52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer.

Peptide compounds useful in the invention may also be prepared using recombinant DNA techniques, using methods now known in the art. See, e.g., Sambrook et al., *Molecular Cloning: A Laboratory Manual*, 2d Ed., Cold Spring Harbor (1989). Non-peptide compounds useful in the present invention may be prepared by art-known methods.

The compounds referenced above may form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluene-sulfonic acid, maleic acid, fumaric acid succinic acid and tartaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Formulation and Administration

Compositions useful in the invention may conveniently be provided in the form of formulations suitable for parenteral (including intravenous, intramuscular and subcutaneous) or nasal or oral administration or suitably encapsulated or otherwise prepared by art-known methods for oral administration. A suitable administration format may best be determined by a medical practitioner for each patient individually. Pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parental Science and Technology*, Technical Report No. 10, Supp. 42:2S (1988).

Compounds useful in the invention can be provided as parenteral compositions for injection or infusion can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

Preferably, these parenteral dosage forms are prepared according to the commonly owned patent application entitled, "Parenteral, Liquid Formulations for Amylin Agonist Peptides," Serial No. 60/035,140, filed Jan. 8, 1997, which is incorporated herein by this reference, and include approximately 0.01 to 0.5% (w/v), respectively, of a compound in an aqueous system along with approximately 0.02 to 0.5% (w/v) of an acetate, phosphate, citrate or glutamate buffer to obtain a pH of the final composition of approximately 3.0 to 6.0 (more preferably 3.0 to 5.5), as well as approximately 1.0 to 10% (w/v) of a carbohydrate or polyhydric alcohol tonicifier in an aqueous continuous phase. Approximately 0.005 to 1.0% (w/v) of an antimicrobial preservative selected from the group consisting of m-cresol, benzyl alcohol, methyl, ethyl, propyl and butyl parabens and phenol is also present in the preferred formulation of product designed to allow the patient to withdraw multiple doses. A sufficient amount of water for injection is used to obtain the desired concentration of solution. Sodium chloride, as well as other excipients, may also be present, if desired. Such excipients, however, must maintain the overall stability of the peptide. Most preferably, in the formulation for parenteral administration, the polyhydric alcohol is mannitol, the buffer is an acetate buffer, the preservative is approximately 0.1 to 0.3 w/v % of m-cresol, and the pH is approximately 3.7 to 4.3.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of a compound of the present invention, for example, a compound which will be effective in one or multiple doses to provide a therapeutic effect at the selected level. Therapeutically effective amounts of a compound of the present invention for use in the control of hyperglycemia, including hyperglycemia associated with insulin resistance, are those that significantly lower post-prandial glucose levels with respect to control, as may be measured by comparing the area under the curve of postprandial glucose concentrations. As will be recognized by those in the field, an effective amount of therapeutic agent will vary with many factors including the age and weight of the patient, the patient's physical condition, the action to be obtained and other factors.

The effective single, divided or continuous doses of the compounds will typically be in the range of 1 $\mu$g/kg/day to about 100 $\mu$g/kg/day, preferably about 0.1 $\mu$g/kg/day to about 10 $\mu$g/kg/day, administered in a single dose or multiple doses.

As will be recognized by those in the field, an effective amount of therapeutic agent will vary with many factors including the age and weight of the patient, the patient's physical condition and other factors. Orally active compounds may be taken orally, however, dosages should be increased 5–10 fold, or should be increased (or decreased) in the ratio described earlier.

To assist in understanding the present invention, the following Examples are included which describe the results of several experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Preparation of Compound 1

Compound 1, having the following formula:

Leu-Ser-Thr-Cys-Val-Leu-Gly-Arg-Leu-Ser-Gln-Glu-Leu-His-Arg-Leu-Gln-Thr-Tyr-Pro-Arg-Thr-Asn-Thr-Gly-Ser-Asn-Thr-Tyr [SEQ.ID.NO. 1]

was assembled on 4-(2'-4'-dimethoxyphenyl-Fmoc-aminomethyl)-phenoxy acetamidonorleucyl norleucine MBHA resin (Novabiochem, 0.44 mmole/g) using Fmoc-protected amino acids (Applied Biosystems, Inc.). Single-coupling cycles were used throughout the synthesis and Fast Moc (HBTU activation) chemistry was employed. The completed peptide resin was deprotected and cleaved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in GAA and lyophilized. The lyophilized peptide was dissolved in water). Crude purity was about 55%.

Used in purification steps were Solvent A (0.1% TFA in water) and Solvent B (0.1% TFA in ACN).

The solution containing peptide was applied to a preparative C-18 column and purified (10% to 40% Solvent B in Solvent A over 40 minutes). The peptide had an observed retention time of 31 minutes. Purity of fractions was determined isocratically using a C-18 analytical column. Pure fractions were pooled furnishing the above-identified peptide. Yield was 84.2 mg (10.2% of theoretical). Analytical RP-HPLC (gradient 20% to 50% Solvent B in Solvent A over 20 minutes) of the lyophilized peptide gave product peptide having an observed retention time of 17.5 minutes. Electrospray Mass Spectrometry (M): calculated 3308.7; found 3308.0.

EXAMPLE 2

Preparation of Compound 2

Compound 2, having the following formula:

4-methylpentanoyl-Ser-Thr-Ala-Val-Leu-Aib-Lys(For)-Leu-Ser-
   Gln-Glu-Leu-Aib-Lys(For)-Leu-Gln-Thr-Tyr-Pro-Arg-Thr-Asn-
   Thr-Gly-Ser-Gly-Thr-Pro                         [SEQ.ID.NO. 2]

was prepared in a similar way as that described in Example 1 except the N-terminal isocaproyl group was incorporated using isocaproic acid in the final synthesis cycle. Preparative RP-HPLC was performed using a C-18 column (25% to 45% Solvent B in Solvent A over 40 minutes). The peptide had an observed retention time of 22 minutes. Analytical RP-HPLC (30% to 50% Solvent B in Solvent A over 20 minutes) gave product peptide with a retention time of 18.7 minutes. Electrospray Mass Spectrometry [M+H]$^+$: calculated 3114.7; found 3114.7.

EXAMPLE 3

Preparation of Compound 3

Compound 3, having the following formula:

Ac-Leu-Ser-Thr-Ser-Val-Leu-Gly-Arg-Leu-Ser-Gln-Glu-LeuHis-
   Arg-Leu-Gln-Thr-Tyr-Pro-Arg-Thr-Asn-Thr-Gly-Ser-Asn-Thr-
   Tyr                                             [SEQ.ID.NO. 3]

was prepared in a similar way as that described in Example 1. Acetylation was accomplished using acetic anhydride. Preparative RP-HPLC was performed using a C-18 Supelco LC-18OB (21×250 mm) column with a flow rate of 200 mL/min (25% to 45% Solvent B in Solvent A over 20 minutes) to give peptide having an observed retention time of 17 minutes. Analytical RP-HPLC (20% to 50% Solvent B in Solvent A over 20 minutes) gave product peptide with a retention time of 16.7 minutes. FAB Mass Spectrometry [M+H]$^+$: calculated 3277.6; found 3278.3.

EXAMPLE 4

Preparation of Compound 4

Compound 4, having the following formula:

Leu-Ser-Thr-Ala-Val-Leu-Gly-Arg-Leu-Ser-Gln-Glu-Leu-His-Arg-
   Leu-Gln-Thr-Tyr-Pro-Arg-Thr-Asn-
   Thr-Gly-Ser-Asn-Thr-Tyr                         [SEQ.ID.NO. 4]

was prepared in a similar way as that described in Example 1. Preparative RP-HPLC was performed using a C-18 column such as that described in Example 3 and eluting with a gradient (25% to 45% Solvent B in Solvent A over 20 minutes) to give peptide having an observed retention time of 13 minutes. Analytical RP-HPLC (20% to 50% Solvent B in Solvent A over 20 minutes) gave product peptide having a retention time of 15.05 minutes Electrospray Mass Spectrometry (M): calculated 3276.7; found 3277.8.

EXAMPLE 5

Preparation of Compound 5

Compound 5, having the formula:

Leu-Ser-Thr-Ser-Val-Leu-Gly-Arg-Leu-Ser-Gln-Glu-Leu-His-Arg-
   Leu-Gln-Thr-Tyr-Pro-Arg-Thr-Asn-
   Thr-Gly-Ser-Asn-Thr-Tyr                         [SEQ.ID.NO. 5]

was prepared in a similar way as that described in Example 1. Preparative RP-HPLC way performed using a C-18 column such as that described in Example 3 and eluting with a gradient (25% to 45% Solvent B in Solvent A over 20 minutes) to give peptide having an observed retention time of 14 minutes. Analytical RP-HPLC (20% to 50% Solvent B in solvent A over 20 minutes) gave product peptide having a retention time of 15.5 minutes. Electrospray Mass Spectrometry (M): calculated 3292.7; found 3293.9.

EXAMPLE 6

Preparation of Compound 6

Compound 6 having the following formula:

Ac-Leu-Ser-Thr-Ala-Val-Leu-Gly-Arg-Leu-Ser-Gln-Glu-Leu-His-
   Arg-Leu-Gln-Thr-Tyr-Pro-Arg-Thr-Asn-Thr-Gly-Ser-Asn-Thr-
   Tyr                                             [SEQ.ID.NO. 6]

was prepared in a similar way as that described in Example 1. Acetylation was accomplished using acetic anhydride. Preparative RP-HPLC was performed using a C-18 column as described in Example 1, eluting with a gradient (25% to 45% Solvent B in Solvent A over 20 minutes) to give peptide having an observed retention time of 17 minutes. Analytical RP-HPLC (20% to 50% Solvent B in Solvent A over 20 minutes) gave product peptide having a retention time of 16.91 minutes. Electrospray Mass Spectrometry (M): calculated 3261.6; found 3262.5.

EXAMPLE 7

Preparation of Compound 7

Compound 7 having the following formula:

Ac-Leu-Ser-Thr-Cys-Val-Leu-Gly-Arg-Leu-Ser-Gln-Glu-Leu-His-
   Arg-Leu-Gln-Thr-Tyr-Pro-Arg-Thr-Asn-Thr-Gly-Ser-Asn-Thr-
   Tyr                                             [SEQ.ID.NO. 7]

was prepared in a similar way as that described in Example 1. Acetylation was accomplished is acetic anhydride. Preparative RP-HPLC was performed using a C-8 column as described in Example 1, eluting with a gradient (15% to 30% Solvent B in Solvent A over 40 minutes) to give peptide having an observed retention time of 32 minutes. Analytical RP-HPLC (20% to 50% Solvent B in Solvent A over 20 minutes) to give product peptide having a retention time of 16.83 minutes. Electrospray Mass Spectrometry (M): calculated 3350.8; found 3349.5.

EXAMPLE 8

Preparation of Compound 8

Compound 8 having the following formula:

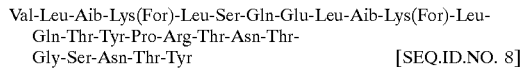

Val-Leu-Aib-Lys(For)-Leu-Ser-Gln-Glu-Leu-Aib-Lys(For)-Leu-Gln-Thr-Tyr-Pro-Arg-Thr-Asn-Thr-Gly-Ser-Asn-Thr-Tyr  [SEQ.ID.NO. 8]

was prepared in a way similar to that described in Example 1. Preparative RP-HPLC was performed using a C-8 column as described in Example 1, eluting with a gradient (25% to 50% Solvent B in Solvent A over 40 minutes) to give peptide having an observed retention time of 12 minutes. Analytical RP-HPLC (20% to 40% Solvent B in Solvent A over 20 minutes) to give product peptide having a retention time of 19.17 minutes. Electrospray Mass Spectrometry (M): calculated 2879.5; found 2879.4.

EXAMPLE 9

Preparation of Compound 9

Compound 9 having the following formula:

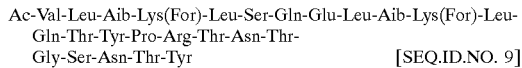

Ac-Val-Leu-Aib-Lys(For)-Leu-Ser-Gln-Glu-Leu-Aib-Lys(For)-Leu-Gln-Thr-Tyr-Pro-Arg-Thr-Asn-Thr-Gly-Ser-Asn-Thr-Tyr  [SEQ.ID.NO. 9]

was prepared in a way similar to that described in Example 1. Acetylation was accomplished using acetic anhydride. Preparative RP-HPLC was performed using a C-8 column as described in Example 1, eluting with a gradient (25% to 50% Solvent B in Solvent A over 40 minutes) to give peptide having an observed retention time of 13 minutes. Analytical RP-HPLC (20% to 50% Solvent B in Solvent A) was performed to give product peptide having a retention time of 14.24 minutes. Electrospray Mass Spectrometry (M): calculated 2921.5; found 2921.1.

EXAMPLE 10

Preparation of Compound 10

Compound 10 having the following formula:

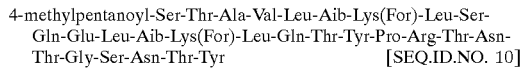

4-methylpentanoyl-Ser-Thr-Ala-Val-Leu-Aib-Lys(For)-Leu-Ser-Gln-Glu-Leu-Aib-Lys(For)-Leu-Gln-Thr-Tyr-Pro-Arg-Thr-Asn-Thr-Gly-Ser-Asn-Thr-Tyr  [SEQ.ID.NO. 10]

is assembled on 4-(2'-4'-dimethoxyphenyl-Fmoc aminomethyl)phenoxyacetamido-norleucyl MBHA resin (Novabiochem, 0.55 mmole/g) using FMOC-protected amino acids (Applied Biosystems, Inc.), cleaved from the resin, deprotected and purified in a similar way to Example 1 except the N-terminal 4-methylpentanoyl group is incorporated using 4-methylpentanoic acid in the final synthesis cycle. Used in analysis are Solvent A (0.1% TFA in water) and Solvent B (0.1% TFA in ACN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 3237.43.

EXAMPLE 11

Preparation of Compound 11

Compound 11 having the following formula:

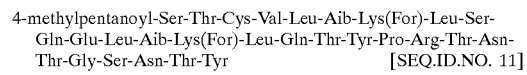

4-methylpentanoyl-Ser-Thr-Cys-Val-Leu-Aib-Lys(For)-Leu-Ser-Gln-Glu-Leu-Aib-Lys(For)-Leu-Gln-Thr-Tyr-Pro-Arg-Thr-Asn-Thr-Gly-Ser-Asn-Thr-Tyr  [SEQ.ID.NO. 11]

is assembled on 4-(2'-4'-dimethoxyphenyl-Fmoc-aminomethyl)phenoxyacetamido-norleucyl MBHA resin (Novabiochem, 0.55 mmole/g) using Fmoc-protected amino acids (Applied Biosystems, Inc.), cleaved from the resin, deprotected and purified in a similar way to Example 1 except the N-terminal 4-methylpentanoyl group is incorporated using 4-methylpentanoic acid in the final synthesis cycle. Used in analysis are Solvent A (0.1% TFA in water) and Solvent B (0.1% TFA in ACN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 3269.49.

EXAMPLE 12

Preparation of Compound 12

Compound 12 having the following formula:

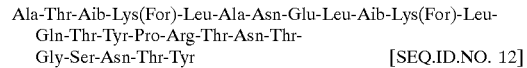

Ala-Thr-Aib-Lys(For)-Leu-Ala-Asn-Glu-Leu-Aib-Lys(For)-Leu-Gln-Thr-Tyr-Pro-Arg-Thr-Asn-Thr-Gly-Ser-Asn-Thr-Tyr  [SEQ.ID.NO. 12]

is assembled on 4-(2'-4'-dimethoxyphenyl-Fmoc aminomethyl)phenoxyacetamido-norleucyl MBHA resin (Novabiochem, 0.55 mmole/g) using Fmoc-protected amino acids (Applied Biosystems, Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2809.89.

EXAMPLE 13

Preparation of Compound 13

Compound 13 having the following formula:

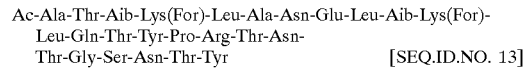

Ac-Ala-Thr-Aib-Lys(For)-Leu-Ala-Asn-Glu-Leu-Aib-Lys(For)-Leu-Gln-Thr-Tyr-Pro-Arg-Thr-Asn-Thr-Gly-Ser-Asn-Thr-Tyr  [SEQ.ID.NO. 13]

is assembled on 4-(2'-4'-dimethoxyphenyl-Fmoc-aminomethyl)phenoxyacetamido-norleucyl MBHA resin (Novabiochem, 0.55 mmole/g) using Fmoc-protected amino acids (Applied Biosystems, Inc.), cleaved from the resin, deprotected and purified in a similar way to Example 1. Acetylation is accomplished using acetic anhydride. Used in analysis are Solvent A (0.1% TFA in water) and Solvent B (0.1% TFA in ACN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2851.92.

EXAMPLE A

Receptor Binding Assays

Receptor binding assays were performed using radioiodinated peptides and membranes from cells or tissues that contain relatively high densities of the receptor to be measured.

Binding of test compounds to amylin receptors was measured by the binding of $^{125}$I-BH-rat amylin ($^{125}$I-Bolton Hunter label on the N-terminal lysine) to membranes from rat nucleus accumbens as set forth below.

Binding of test compounds to CGRP receptors was measured by the binding of $^{125}$I-L-αCGRP ($^{125}$I-labeled at histidine) to membranes from human SK-N-MC neuroblastoma cells.

Binding of test compounds to calcitonin receptors was measured by the binding of $^{125}$I-human calcitonin ($^{125}$I-labeled at tyrosine) to membranes from human MCF7 breast carcinoma cells, which express high densities of adenylyl cyclase-coupled calcitonin receptors. A clonal sub-line (MCF7-7) which was isolated from the parental MCF7 cell line was used in these experiments.

Binding to Rat Nucleus Accumbens Membranes (Amylin Receptors)

Evaluation of the binding of compounds to amylin receptors was carried out as follows. $^{125}$I-BH-rat amylin was purchased from Amersham Corporation (Arlington Heights, Ill.). Specific activities at time of use ranged from 1950 to 2000 Ci/mmol. Unlabeled peptides were obtained from BACHEM Inc. (Torrance, Calif.) and Peninsula Laboratories (Belmont, Calif.).

Male Sprague-Dawley rats (200 to 250 grams) were sacrificed by decapitation. Brains were removed to cold phosphate-buffered saline (PBS). From the ventral surface, cuts were made rostral to the hypothalamus, bounded laterally by the olfactory tracts and extending at a 45° angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23° C.). Membranes were washed three times in fresh buffer by centrifugation for 15 minutes at 48,000×g. The final membrane pellet was resuspended in 20 mM HEPES buffer containing 0.2 mM phenylmethylsulfonyl fluoride (PMSF).

To measure $^{125}$I-amylin binding, membranes from 4 mg original wet weight of tissue were incubated with 125I-amylin at 12 to 16 pM in 20 mM HEPES buffer containing 0.5 mg/ml bacitracin, 0.5 mg/ml bovine serum albumin, and 0.2 mM PMSF. Solutions were incubated for 60 minutes at 23° C. Incubations were terminated by filtration through GF/B glass fiber filters (Whatman Inc., Clifton, N.J.) which had been presoaked for 4 hours in 0.3% poylethyleneimine in order to reduce nonspecific binding of radiolabeled peptides. Filters were washed immediately before filtration with 5 ml cold PBS, and immediately after filtration with 15 ml cold PBS. Filters were removed and radioactivity assessed in a gamma-counter at a counting efficiency of 77%.

Binding to Membranes from SK-N-MC Cells (CGRP Receptors)

SK-N-MC cells (ATCC No. HTB-10) were homogenized in 50 mM Hepes buffer, pH 7.4, and membranes were collected by centrifugation for 15 min at 48000×g. Membranes suspended at a concentration of 0.1 to 0.2 mg protein/0.2 ml aliquot were incubated in 50 mM Hepes, pH 7.4 containing bovine serum albumin, bacitracin, and 2 mM MgCl$_2$ with 15 pM [$^{125}$I]human-CGRP (labeled at $^{10}$His, 2000 Ci/mmol) and unlabeled peptides. Additional methods were similar to those described for amylin receptor assays. K$_i$ was derived as IC$_{50}$/(1+([L]/K$_d$)) where [L] was 15 pM and K$_d$ was 3 pM.

SK-N-MC human neuroblastoma cells have been shown to contain a high-affinity CGRP receptor that is coupled adenylate cyclase and which has binding and specificity characteristics similar to CGRP receptors present in several other tissues (VanValen et al., 1990). K$_i$ values were derived from inhibition of [$^{125}$I]hCGRP binding to membranes from SK-N-MC cells.

Binding to Membranes from T47D Cells (Calcitonin Receptors)

Membranes from human T47D breast carcinoma cells (ATCC No. HTB 133), previously shown to contain high densities of calcitonin receptors (Findlay et al., 1980). Membranes were prepared from confluent cultures of T47D cells as described for SK-N-MC cells. Membranes were incubated with 32 pM [$^{125}$I]salmon calcitonin (labeled at $^{22}$Tyr, 2000 Ci/mmol), and with unlabeled peptides for 60 minutes at ambient temperature. Additional methods are similar to those described for CGRP receptor assays. K$_i$ was derived as IC$_{50}$/(1+([L]/K$_d$)) where [L] was 32 pM and K$_d$ was 19 pM.

Binding to calcitonin receptors as quantified by displacement of [$^{125}$I]salmon calcitonin from membranes in human T47D carcinoma cells.

Results

Certain compounds of the present invention were tested in radioligand binding assays as described above to determine their affinities for amylin, calcitonin and CGRP receptors.

Competition curves were generated by measuring radioligand binding in the presence of increasing concentrations of test compounds with the half-maximal inhibitory concentration (IC$_{50}$) determined using an iterative curve fitting program (nonlinear regression using a 4-parameter logistic equation; Inplot program; Graph PAD Software, San Diego).

TABLE I

Competition for amylin, calcitonin, and CGRP receptors

| Compound No. | Receptor IC$_{50}$ in nM [mean ± SEM (n)] | | |
|---|---|---|---|
| | Amylin | Calcitonin | CGRP |
| 1 | 0.250 ± 0.091(4) | 0.22 + 0.02(3) | 160 ± 42(4) |
| 2 | 12.0 ± 1.3(3) | 0.37 + 0.03(3) | >10,000(1) |
| 3 | 37.0 ± 4.6(2) | 1.45 + 0.04(2) | >10,000(2) |
| 4 | 0.066 ± 0.008(3) | 0.13 + 0.07(2) | 92 ± 13(2) |
| 5 | 0.092 ± 0.011(2) | 0.15 + 0.05(2) | 44 ± 12(2) |
| 6 | 18.6 ± 5.3(4) | 0.56 + 0.02(2) | >10,000(2) |
| 7 | 0.16 ± 0.11(2) | 0.21 + 0.07(2) | 1,400(1) |
| 8 | 23.6(1) | 93(1) | >10,000(1) |
| 9 | 7.6(1) | 24(1) | >10,000(1) |

All test compounds demonstrated relative affinities for amylin (nucleus accumbens) and calcitonin (T47D) receptors, compared with their affinities for CGRP (SK-N-MC) receptors. For example, the test compounds showed at least a 300-fold lower affinity for the CGRP receptors than the amylin receptors. Within the series of compounds, Compounds 1, 4, 5, 7, 8 and 9 showed similar potencies of amylin and calcitonin receptors. Compounds 2, 3 and 6 showed greater affinity for calcitonin receptors than for amylin receptors.

EXAMPLE B

Assay of Adenyl Cyclase Stimulation

Compounds of the present invention were assayed for functional activity at calcitonin receptors using human T47D (ATCC No. HTB 133) and MCF7 (ATCC No. 22) breast carcinoma cells, both of which contain calcitonin receptors coupled to the stimulation of adenyl cyclase activity. For Compound 1, functional activity at rat calcitonin C1a receptors was also determined in HEK293 cells (ATCC No. CRL 1573) which had undergone stable transection with the rat calcitonin C1a receptor.

Cells were grown to confluency in 96 well plates. Medium was removed (by shaking into sink and tapping plate onto tissue). Medium was replaced with 100 µL dPBS (10 mL of 10×Dulbecco's PBS up to 100 mL with water; and 0.1 g FA-free BSA and 0.1 g glucose; pH adjusted to 7.4) containing 0.1% BSA and 0.1% glucose. Cells were incubated in an air incubator for 20 to 30 minutes at 37° C. Medium was replaced with fresh dPBS containing 0.5 mM IBMX (4.5 mg IBMX was added into 50 mL modified dPBS; mixture was sonicated until IBMX was in solution). Cells were incubated 10 minutes. Hormone and/or test compound was diluted into dPBS medium containing IBMX. A 100 µL aliquot of hormone (or test compound) solution was added to plates. Cells were incubated for 20 to 30 minutes at 37° C. in a humidified air incubator. The reaction was stopped by addition of 20 µL of 5% TCA. Plates containing cells were kept at 4° C. for 15 minutes. A 20 µL aliquot of 0.8 M Trizma was added to neutralize media. Plates were agitated, then spun at 2000 rpm in a floor centrifuge. Supernatant was decanted and directly used in acetate buffer in a standard cAMP radioimmunoassay.

In breast carcinoma cells, human calcitonin stimulated increases in cyclic AMP accumulation with an $EC_{50}$ of 0.45 nM (MCF7-7) and 3.1 jnM (T47D). Human amylin was 5-fold (MCF7-7) to 7-fold (T47D) less potent than calcitonin in stimulating adenyl cyclase activity in these cells. FIG. 1 depicts the effect of Compound 1 on cyclic AMP production in T47D cells. Compound 1 strongly stimulated cyclic AMP accumulation in T47D cells, with an $EC_{50}$ of 2.2 nM as shown in FIG. 1. In these cells, Compound 1 was somewhat more potent that human calcitonin in stimulating adenylyl cyclase activity. Thus, Compound 1 are functional agonists at calcitonin receptors in human cells. Compound 1 was also tested in cells expressing rat calcitonin C1a receptors, and again strongly stimulated adenyl cyclase activity, with an $EC_{50}=0.97$ nM (data not shown).

Compound 2 was also tested for functional activity at calcitonin receptors. Compound 2 had partial agonist activity in MCF7-7 cells, producing an increase in cyclic AMP that was approximately 20% of the increase production by human calcitonin. Compound 2 had an $EC_{50}$ of 1.6 nM (3.5-fold less potent than human calcitonin) in producing this effect.

Compound 4 ($EC_{50}=3.5$ nM) and Compound 6 ($EC_{50}=34$ nM) were also tested in this assay and were observed to stimulate adenylyl cyclase activity in MCF7-7 cells, with 7-fold and 80-fold lower potency than human calcitonin.

EXAMPLE C

Soleus Muscle Assay

Determination of amylin antagonist activity of test compounds in the soleus muscle assay was carried out as follows. Male Harlan Sprague-Dawley rats of approximately 200 g mass were used in order to maintain mass of the split soleus muscle less than 40 mg. The animals were fasted for 4 hours prior to sacrifice by decapitation. The skin was stripped from the lower limb which was then pinned out on corkboard. The tendo achilles was cut just above os calcis and m. gastrocnemius reflected out from the posterior aspect of the tibia. M. soleus, a small 15–20 mm long, 0.5 mm thick flat muscle on the bone surface of m. gastrocnemius was then stripped clear and the perimysium cleaned off using fine scissors and forceps. M. soleus was then split into equal parts using a blade passed antero-posteriorly through the belly of the muscle to obtain a total of 4 muscle strips from each animal. After dissecting the muscle from the animal, it was kept for a short period in physiological saline. It was not necessary that the muscle be held under tension as this had no demonstrable effects on radioglucose incorporation into glycogen.

Muscles were added to 50 mL Erlenmeyer flasks containing 10 mL of a pregassed Krebs-Ringer bicarbonate buffer containing (each liter) NaCl 118.5 mmol (6.93 g), KCl 5.94 mmol (443 mg), $CaCl_2$ 2.54 mmol (282 mg), $MgSO_4$ 1.19 mmol (143 mg), $KH_2PO_4$ 1.19 mmol (162 mg), $NaHCO_3$ 25 mmol (2.1 g), 5.5 mmol glucose (1 g) and recombinant human insulin (Humulin-R, Eli Lilly, Ind.) and the test compound, as detailed below. The pH at 37° C. was verified as being between 7.1 and 7.4. Muscles were assigned to different flasks so that the 4 muscle pieces from each animal were evenly distributed among the different assay conditions. The incubation media were gassed by gently blowing carbogen (95% $O_2$, 5% $CO_2$) over the surface while being continuously agitated at 37° C. in an oscillating water bath. After a half-hour "preincubation" period, 0.5 µCi of U-$^{14}$C-glucose was added to each flask which was incubated for a further 60 minutes. Each muscle piece was then rapidly removed, blotted and frozen in liquid $N_2$, weighed and stored for subsequent determination of $^{14}$C-glycogen.

$^{14}$C-glycogen determination was performed in a 7 mL scintillation vial. Each frozen muscle specimen was placed in a vial and digested in 1 mL 60% potassium hydroxide at 70° C. for 45 minutes under continuous agitation. Dissolved glycogen was precipitated out onto the vial by the addition of 3 mL absolute ethanol and overnight cooling at −20° C. The supernatant was gently aspirated, the glycogen washed again with ethanol, aspirated and the precipitate dried under vacuum. All ethanol is evaporated.to avoid quenching during scintillation counting. The remaining glycogen was redissolved in 1 mL water and 4 mL scintillation fluid and counted for $^{14}$C.

The rate of glucose incorporation into glycogen (expressed in µmol/g/hr) was obtained from the specific activity of $^{14}$C-glucose in the 5.5 mM glucose of the incubation medium, and the total $^{14}$C counts remaining in the glycogen extracted from each muscle. Dose/response curves were fitted to a 4-parameter logistic model using a least-squares iterative routine (ALLFIT, v2.7, NIH, MD) to derive $EC_{50}$s. Because $EC_{50}$ is log-normally distributed, it is expressed ± standard error of the logarithm. Pairwise comparisons were performed using t-test based routines of SYSTAT (Wilkinson, "SYSTAT: the system for statistics," SYSTAT Inc., Evanston Ill. (1989)).

Dose response curves were generated with muscles added to media containing 7.1 nM (1000 µU/mL) insulin and each test compound added at final (nominal) concentrations of 0, 1, 3, 10, 30, 100, 300 and 1000 nM. Each assay also contained internal positive controls consisting of a single batch of archived rat amylin, lyophilized and stored at −70° C.

$EC_{50}$ measurements of amylin preparations in the soleus muscle assay range typically from about 1 to 10 nM, although some commercial preparations which are less than 90% pure have higher $EC_{50}$s presumably due to the presence of contaminants that result in a lower measured activity. Results for test compounds are set forth below and in FIGS. 2 and 3.

In the isolated, incubated, rat soleus muscle preparation, Compound 1 and Compound 2 exhibited no discernable amylin agonist activity in inhibition of incorporation of glucose into glycogen. In this assay insulin increases the incorporation of $^{14}C$, derived from $^{14}C$-labeled glucose in the incubation medium, into glycogen by a factor of 3–4 over a period of 1 hour. The glycogen is subsequently extracted from incubated soleus muscle strips and analyzed. In this assay, amylin action is typified by a reduction in incorporation of the $^{14}C$ from glucose into glycogen (shown herein FIG. 2 in the presence of insulin). The antagonism of amylin action is thus indicated by the prevention of the amylin-mediated reduction of incorporation of $^{14}C$ into glycogen.

Figure 2A:
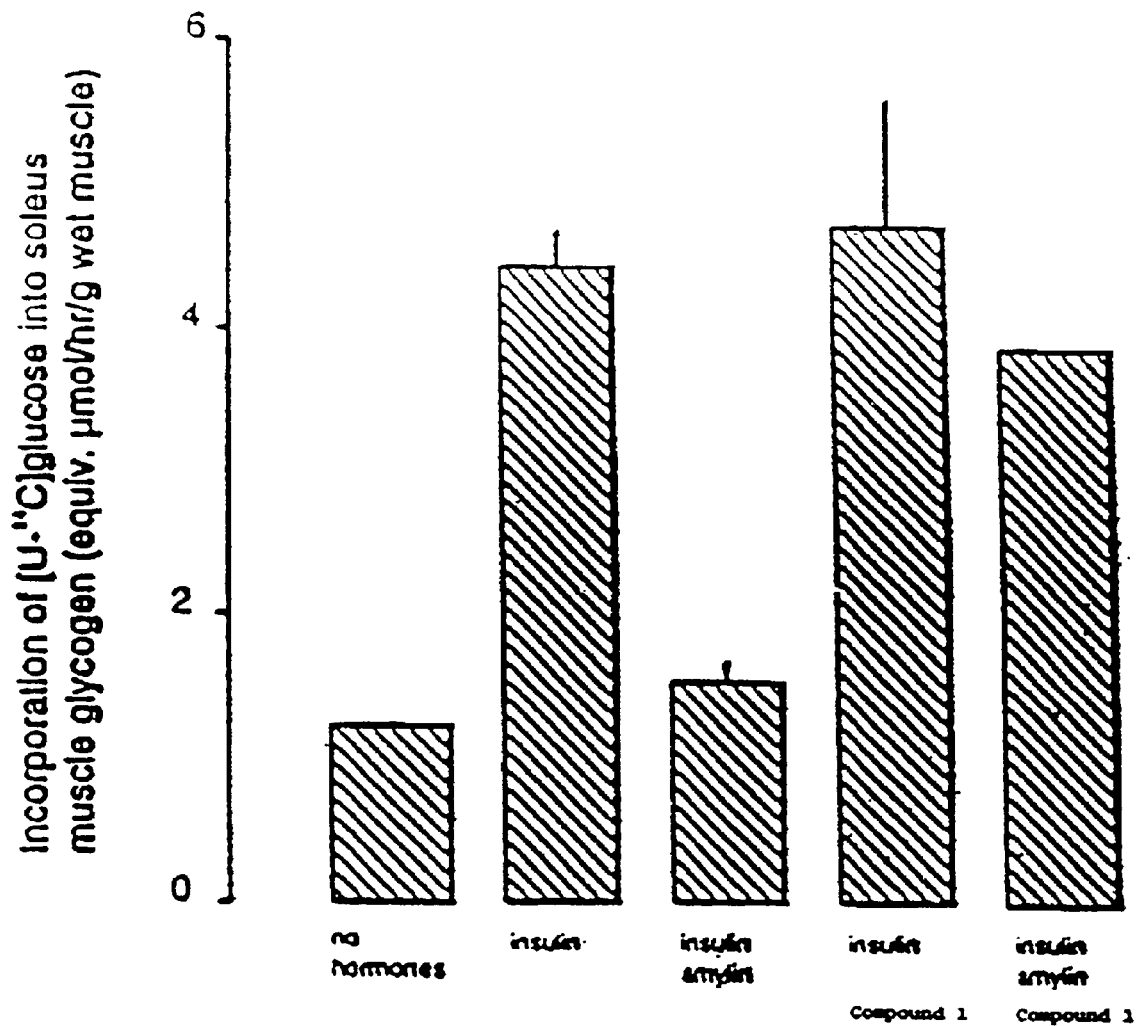
FIGS. 2A and 2B depict in vitro amylin antagonist activity of Compound 1 (FIG. 2A) and the compound of Example 2 ("Compound 2") [SEQ.ID.NO. 2] (FIG. 2B) in the soleus muscle assay.
Figure 2B:
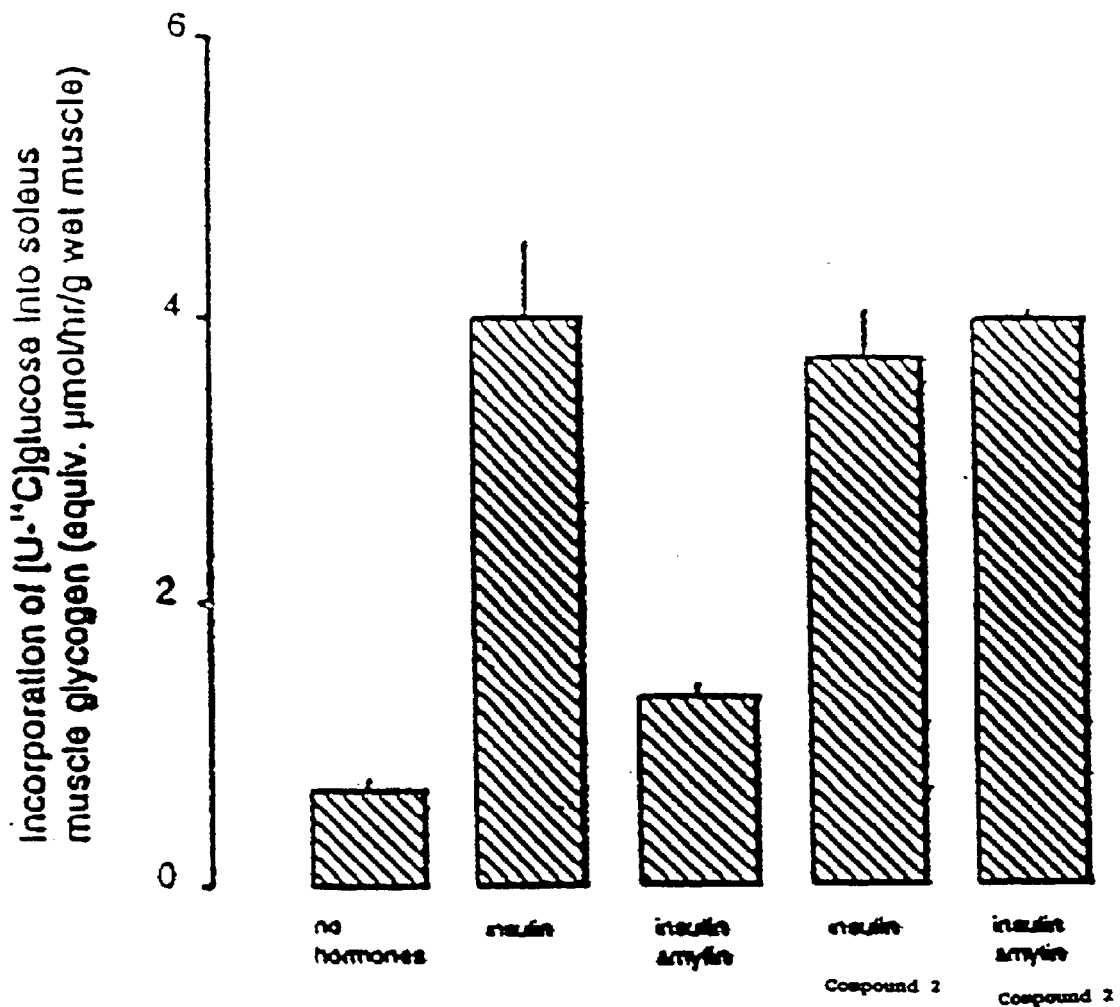

Results of experiments with Compound 1 and Compound 2 are shown in FIGS. 2A and 2B. FIGS. 2A depicts results with Compound 1 and FIG. 2B depicts results with Compound 2. The second bar in each figure shows the stipulatory effect of insulin (1000 μUnits/ml, 7.1 nM) on $^{14}C$ incorporation from $^{14}C$-glucose. The third bar in each figure shows the effect of amylin (100 nM) in reducing the insulin-stimulated $^{14}C$ incorporation from $^{14}C$-glucose to values near to those observed in the absence of insulin. The fourth bar in each figure shows that neither Compound 1 (100 nM) nor Compound 2 (100 nM) affected the response to insulin. That is, neither Compound 1 nor Compound 2 displayed amylin agonist activity in this assay. In the fifth set of bars, the effect of amylin (100 nM) on insulin-stimulated incorporation of glucose into glycogen (7.1 nM) (as shown in the third set of bars) is reversed by the addition of either Compound 1 (1 μM) or Compound 2 (1 μM) That is, Compound 1 and Compound 2 displayed amylin antagonist activity in this assay.

Figure 3:
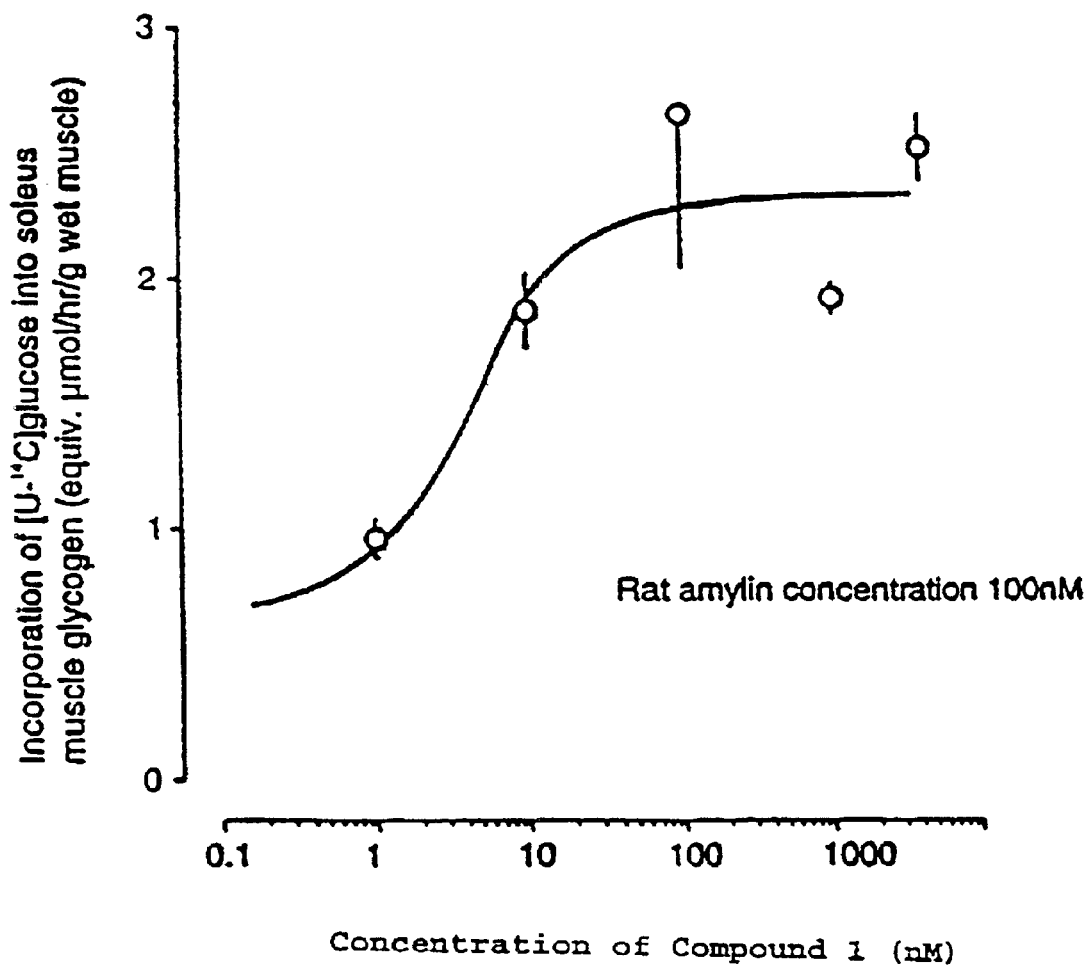
FIG. 3 depicts a dose response curve for amylin antagonist activity of Compound 1 measured in the soleus muscle assay. Reversal of the effects of rat amylin on insulin-stimulated incorporation of $^{14}$C-glucose in isolated soleus muscle at varying doses of test compound is shown.

FIG. 3 depicts a dose response curve for the reversal by Compound 1 of the effects of rat amylin (100 nM) on insulin-stimulated incorporation of $^{14}C$ into glycogen from $^{14}C$-glucose in isolated soleus muscle. The $IC_{50}$ value from the graph is about 4 nM for Compound 1.

EXAMPLE D

Effect on Plasma Glucose, Lactate and Calcium Levels

Male Harlan Sprague Dawley rats were housed at 22.7°±0.8° C. in a 12:12 hour light:dark cycle (experiments being performed during the light cycle) and fed and watered ad libitum (Diest LM-485, Teklad, Madison, Wis.). Animals used were aged 87–94 days and weighed 353–392 g. They were deprived of food for –20 hours prior to experimentation.

Anesthesia was induced with 5% halothane, maintained at 2% during surgery and at 0.8–1% during recordings. Tracheotomy and cannulation of the right femoral artery and saphenous vein were performed. The femoral arterial line was connected to a pressure transducer (Spectramed P23XL transducer, Model 13-4615-58 amplifier, Gould, Cleveland, Ohio) and perfused with heparinized saline (2 U.mL) at 3.0 mL/hr. Colonic temperature was measured using a thermistor probe and controller (Model 73A, YSI, Yellow Springs, Ohio) which provided closed-loop control of core temperature by switching a heated operating table. The signal for mean arterial pressure was periodically sampled and stored with 12-bit precision at 1 Hz using a computerized data acquisition system (DT2801A A.D converters, Data Translation, Marlboro, Mass.; AST Premium 386 computer, AST Research, Irvine, Calif.; Labtech Notebook software, Laboratory Technologies Corp, Wilmington, Mass.).

Synthetic rat amylin (Bachem, Torrance, Calif.) was tested for its ability to bind in the amylin receptor assay, and for bioactivity using the soleus muscle assay. The test compounds were made by solid phase peptide synthesis as described above.

The following treatment groups were utilized: (1) control rats (n=5) which, at t=0, were injected subcutaneously with 0.1 mL of 0.15M saline; (2) amylin injection rats (n=5) which at t=0, were administered 100 μg synthetic rat amylin in 0.1 mL saline as a subcutaneous bolus into the ventral abdominal wall; and (3) amylin injection following test compound preinfusion rats (n=1). In group 3, subcutaneous amylin injection (as in Group 2) was preceded by a primed/continuous intravenous infusion of test compounds. A bolus intravenous dose of 0.5 mg of test compound at –30 min was followed by a 1 mg/hr intravenous infusion of test compound until t=120 min.

Arterial samples of 250 μL were drawn into non-heparinized Natelson tubes at –30, –15, 0, 15, 30, 45, 60, 90 and 120 minutes (relative to amylin injection), transferred to chilled EDTA microphage tubes, spun, and the separated plasma analyzed immediately for glucose and lactate using immobilized enzyme chemistries (glucose oxidase, L-lactate oxidase, Analyzer model 2300-STAT, YSI, Yellow Springs, Ohio).

Total plasma calcium was measured using a dye-binding assay (o-cresolphthalein complexone, Sigma procedure 587; Sigma, St. Louis, Mo., USA).

The response to subcutaneous injections of 100 μg of Compound 1 or Compound 2 were compared to those obtained with either 100 μg of rat amylin or a saline vehicle control. Plasma glucose and lactate concentrations typically have been observed to increase following rat amylin injections. This response to amylin has been interpreted as being at least partly due to amylin-mediated glycogenolysis, release of lactate from muscle and subsequent gluconeogenesis from the released lactate. In addition, plasma calcium levels are typically observed to fall; this effect may be due to amylin action at calcitonin receptors.

Figure 4A:
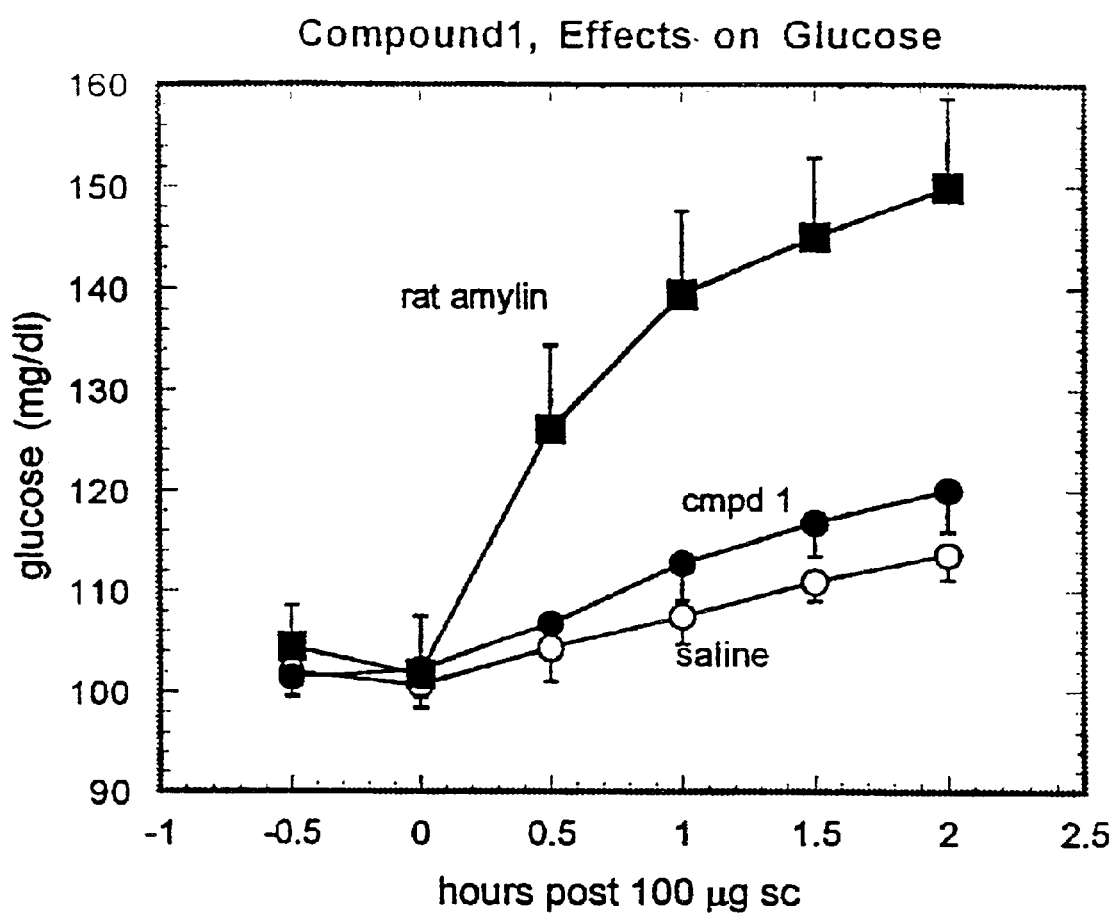
FIGS. 4A to 4C depict the in vivo activity of Compound 1 on plasma glucose levels (FIG. 4A), plasma lactate levels (FIG. 4B) and plasma calcium levels (FIG. 4C) in anesthetized rats.
Figure 4B:
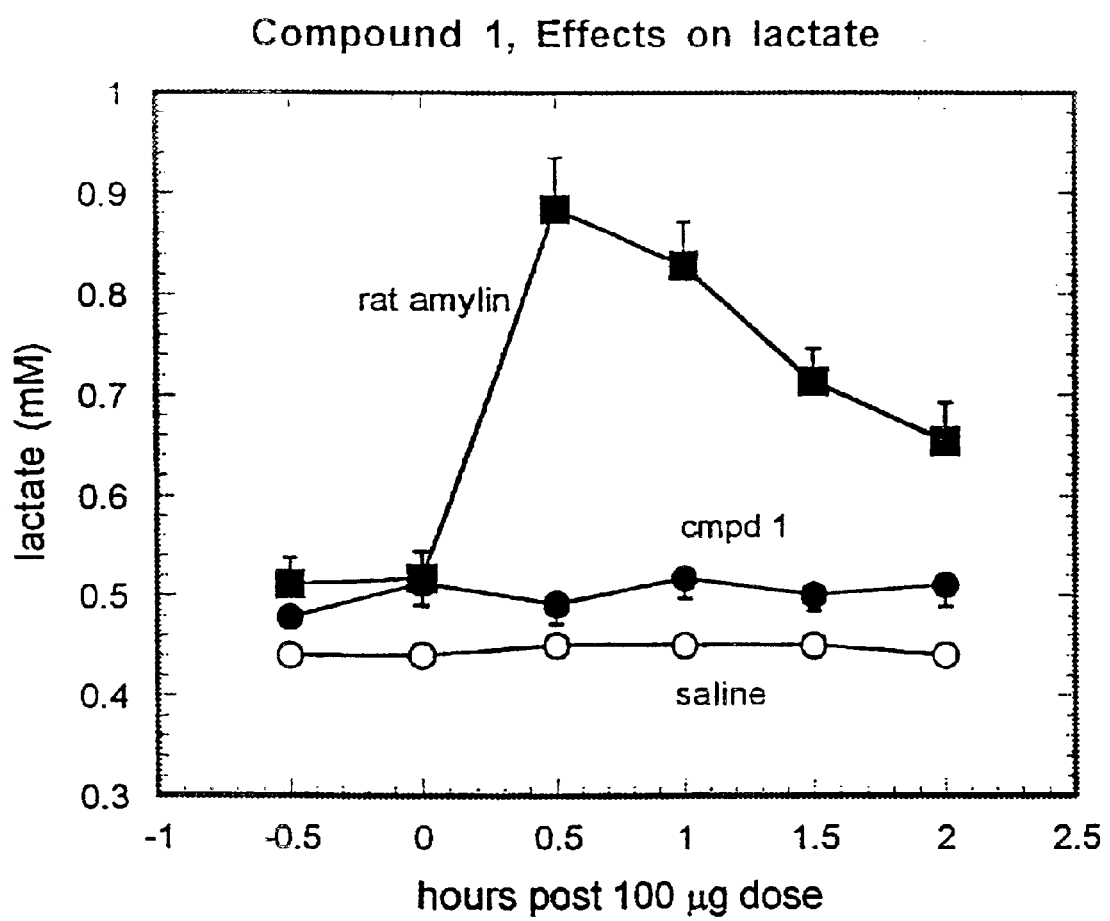
Figure 4C:
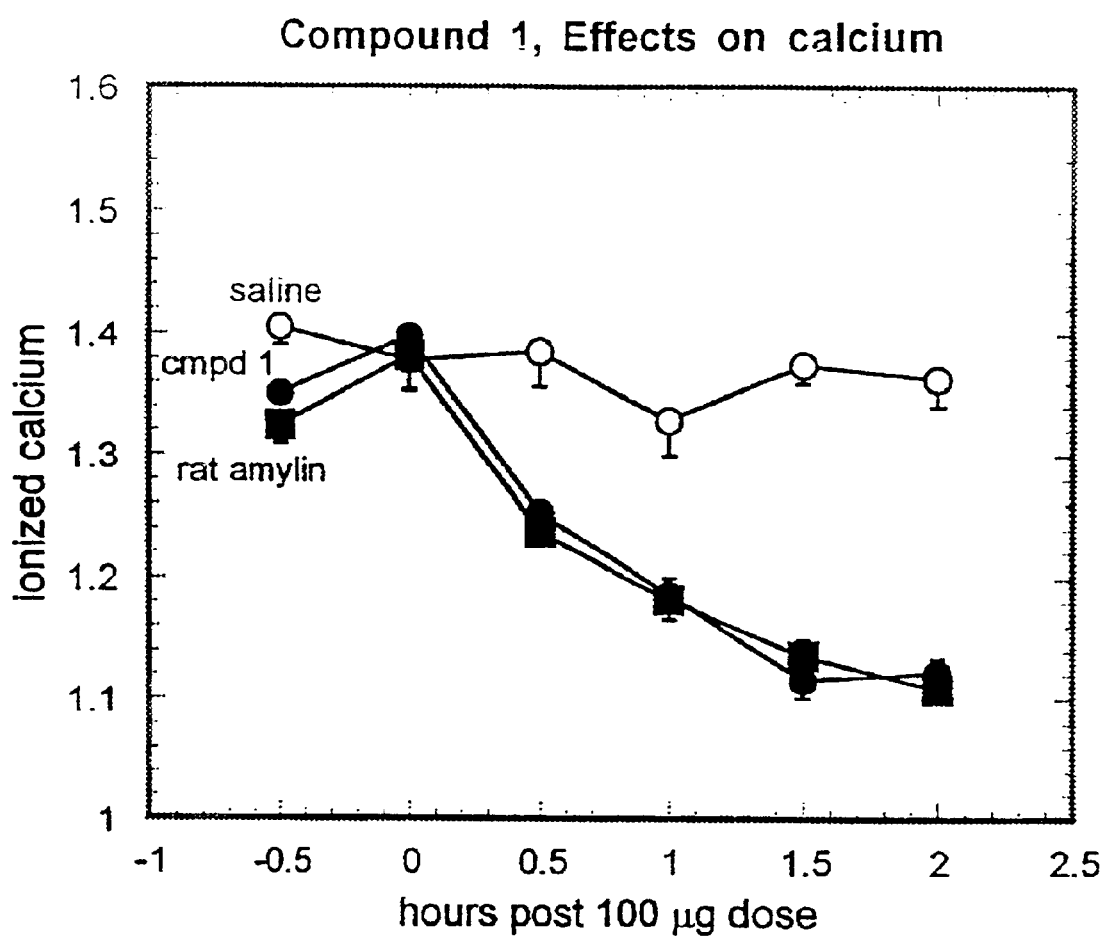
Figure 5A:
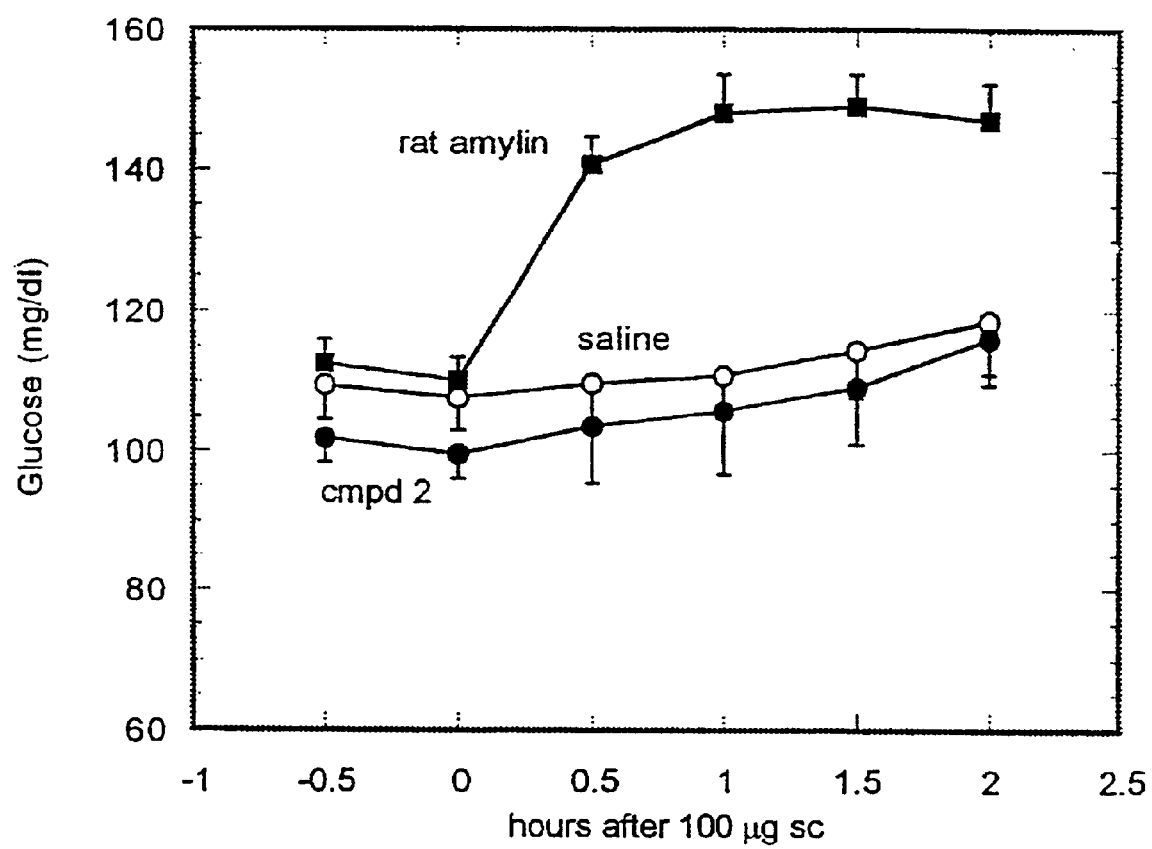
FIGS. 5A to 5C depict the in vivo activity of Compound 2 on plasma glucose levels (FIG. 5A), plasma lactate levels (FIG. 5B) and plasma calcium levels (FIG. 5C) in anesthetized rats.
Figure 5B:
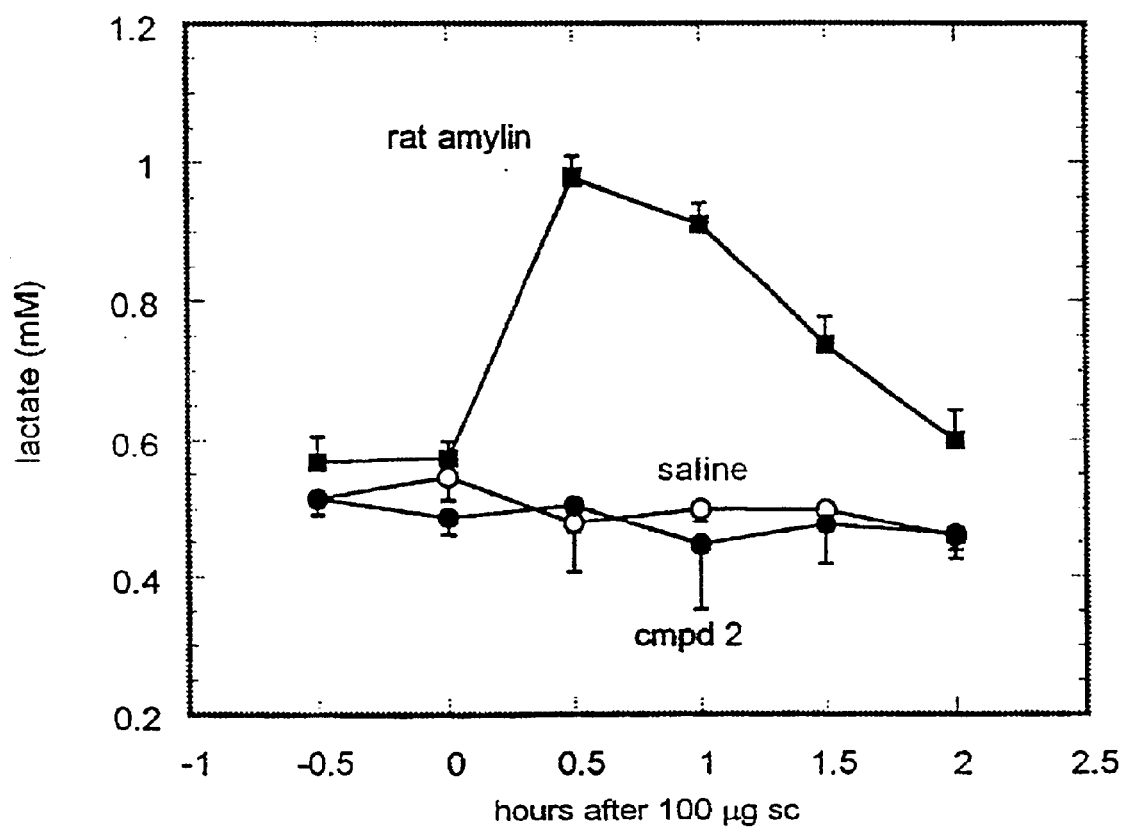
Figure 5C:
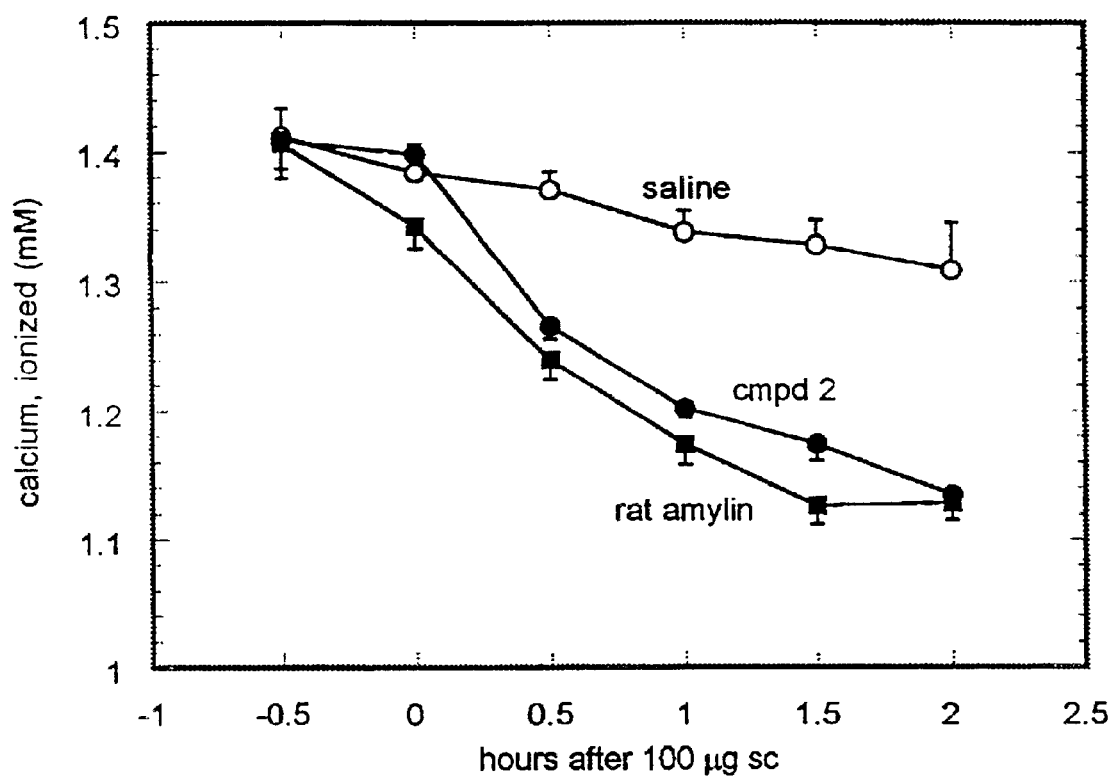
Figure 6A:
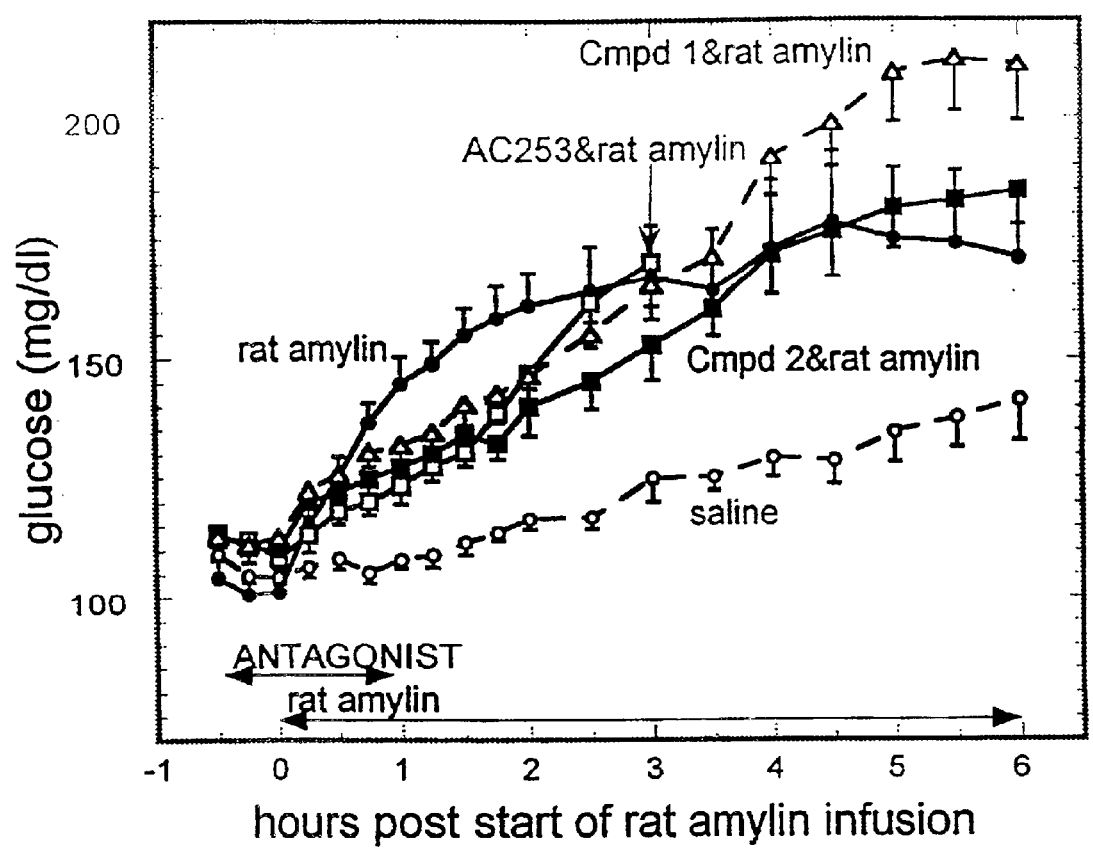
FIGS. 6A to 6C depict in vivo activity of Compound 1 and Compound 2 in inhibiting effects of rat amylin on plasma levels of glucose (FIG. 6A), lactate (FIG. 5B) and calcium (FIG. 6C) in anesthetized rats. Also measured was mean arterial pressure (FIG. 6D).
Figure 6B:
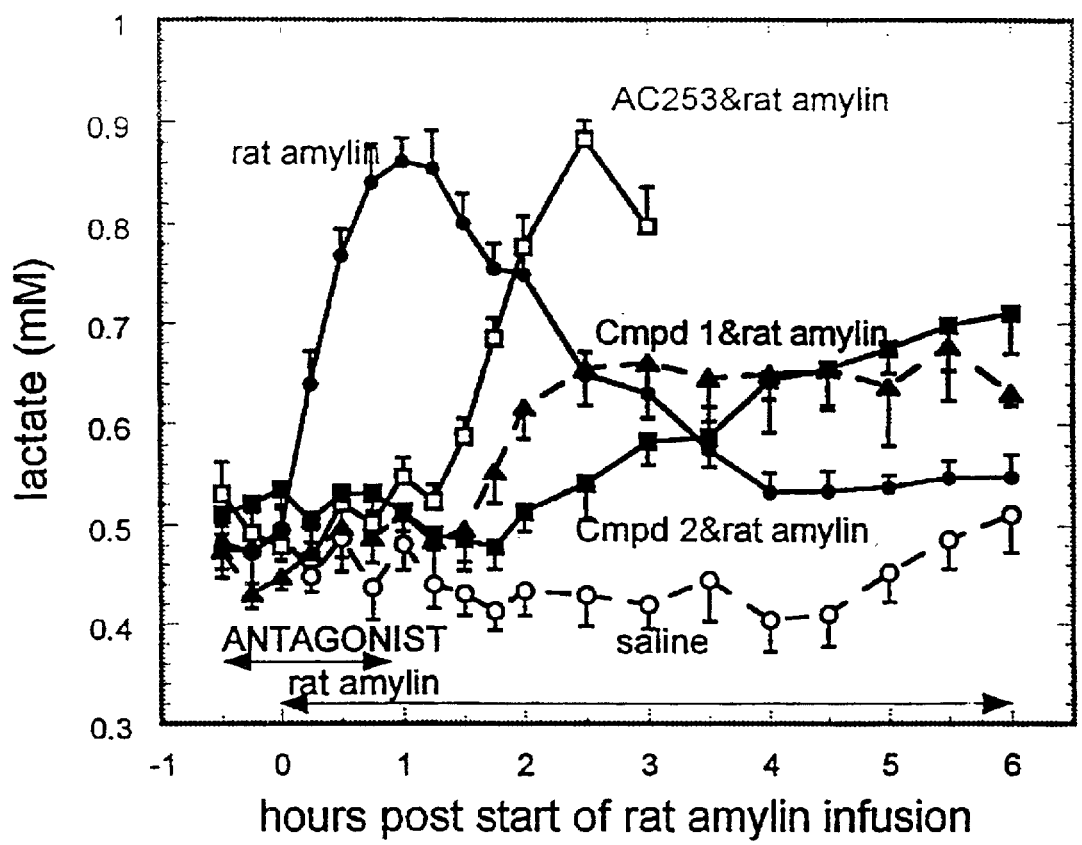
Figure 6C:
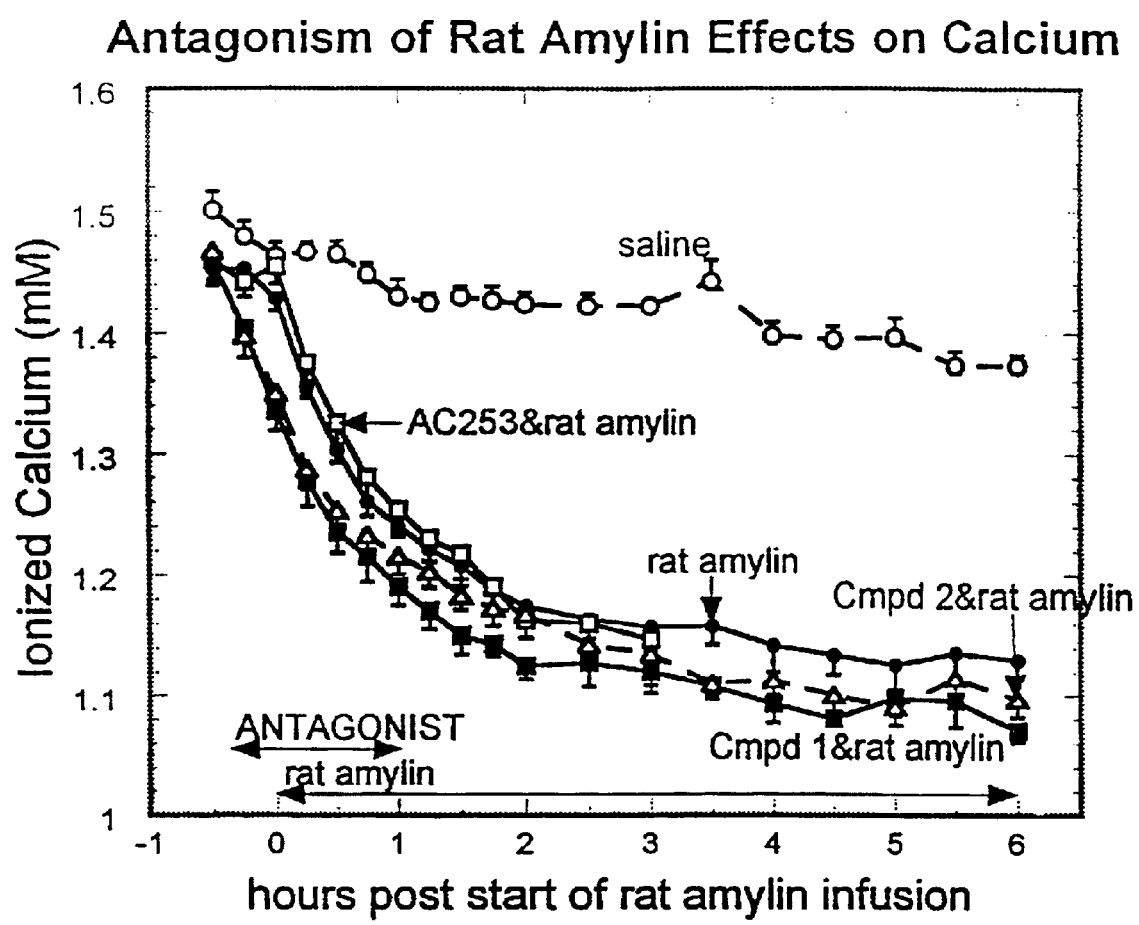
Figure 6D:
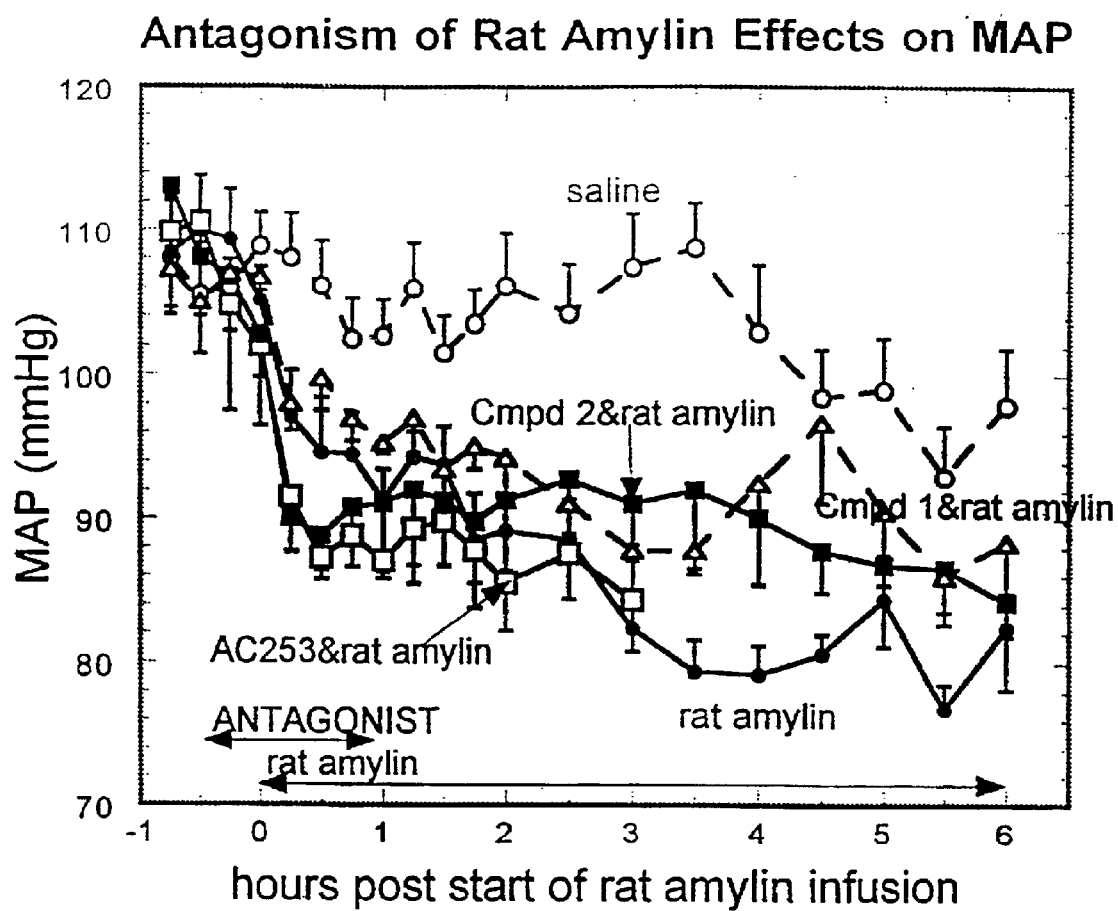

FIGS. 4A to 4C depict the response of plasma glucose (FIG. 4A), lactate (FIG. 4B) and calcium (FIG. 4C) levels in anesthetized rats following subcutaneous injection of Compound 1 compared to such levels following injection of rat armylin or a saline vehicle control. FIGS. 5A to 5C show the response of plasma glucose (FIG. 5A), lactate (FIG. 5B) and calcium FIG. 5C) levels in anaesthetized rats following injection of Compound 2 compared to such levels following injection of rat amylin or saline vehicle control.

As depicted in FIGS. 4A to 4C and 5A to 5C, neither Compound 1 nor Compound 2 increased either plasma lactate or plasma glucose, a result consistent with their lack of amylin agonism observed in the soleus muscle assay (see Example C). Compounds 1 and 2 caused a fall in plasma calcium concentration, which was consistent with their activities as a calcitonin agonists.

EXAMPLE E

Effect on Plasma Glucose, Lactate and Calcium Levels, in the Presence of Amylin

Male Harlan Sprague Dawley rats (age 75 to 85 days, mass 300–350 g) fasted 18 to 20 hours were halothane anesthetized and cannulated via the saphenous vein for infusions/injections and via the femoral artery for sampling of glucose/lactate/calcium and for recording arterial pressure. Heart rate was also monitored via ECG.

One and a half hours after surgery the rats were infused with a 1.5 mg bolus of Compound 2 followed by an infusion of 3 mg/hour for an additional 1.5 hours (t=0.5 to 1.0 hour). At t=0 hours (0.5 hours after the start of the primed/continuous test compound infusion) a 50 µg bolus of rat amylin was administered followed by an infusion of 50 µg/hour of rat amylin which continued until the end of the experiment. Blood samples were collected every 10 minutes for the first 2 hours of the test and then every 30 minutes. Mean arterial pressure and heart rate were continuously recorded from t=0.5 to t=+5 hours. The study was terminated at t=6 hours. A previously reported amylin antagonist, AC253 (Prickett, K. S. et al., "Design of Receptor Selection Peptides that Antagonize the Actions of Amylin In Vivo", *Peptides Chemistry Structure and Biology* (Kaumaya and Hodges, eds.), pages 620 to 622 (1996), was included as a positive control.

FIGS. 6A to 6D depict the effects of Compound 1 and Compound 2 on plasma glucose (FIG. 6A), plasma lactate (FIG. 6B), plasma calcium (FIG. 6C) and mean arterial pressure (FIG. 6D) as a function of time after amylin administration. In this protocol, rat amylin antagonist activity is indicated by the suppression of the increases in plasma glucose and lactate which typically follow amylin administration. Preinfusions with Compound 1 or Compound 2 resulted in smaller increases in lactate and glucose levels than those observed in control rats preinfused with saline alone, which indicates that these compounds antagonized the hyperlacemic and hyperglycemic actions of amylin in vivo. A fall in plasma calcium levels began after infusion of Compound 1 or Compound 2 and was not changed by the subsequent amylin infusion. This observed effect on plasma calcium is considered typical of amylin and calcitonin agonist activity. The lack of ability of these compounds to reverse the blood pressure lowering effect of amylin, an effect known to be mediated through CGRP receptors, demonstrates the selective activity of the test compounds.

EXAMPLE F

Phenol Red Gastric Emptying Assay

Gastric emptying was measured using a modification (Plourde et al., Life Sci. 53:857–862 (1993)) of the original method of Scarpignato et al. (Arch. Int. Pharmacodyn. Ther. 246:286–295 (1980)). Conscious rats received by gavage. 1.5 mL of an a caloric gel containing 1.5% methyl cellulose (M-0262, Sigma Chemical Co., St. Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In most experiments, the stomach was clear. In other experiments, particulate gastric contents were centrifuged to clear the solution for absorbance measurements. Where the diluted gastric contents remained turbid, the spectroscopic absorbance due to phenol red was derived as the difference between that present in alkaline versus acidified diluent. In separate experiments on 7 rats, the stomach and small intestine were both excised and opened into an alkaline solution. The quantity of phenol red that could be recovered from the upper gastrointestinal tract within 29 minutes of gavage was 89±4%; dye which appeared to bind irrecoverably to the gut luminal surface may have accounted for the balance. To compensate for this small loss, percent of stomach contents remaining after 20 minutes were expressed as a fraction of the gastric contents recovered from control rats sacrificed immediately after gavage in the same experiment. Percent gastric emptying contents remaining=(absorbance at 20 min)/(absorbance at 0 min). Dose response curves for gastric emptying were fitted to a 4-parameter logistic model using a least-squares iterative routine (ALLFIT, v2.7, NIH, Bethesda, Md.) to derive $ED_{50}$s. Because $ED_{50}$ is log-normally distributed, it is expressed ± standard error of the logarithm. Pairwise comparisons were performed using one-way analysis of variance and the Student-Newman-Keuls multiple comparisons test (Instat v2.0, GraphPad Software, San Diego, Calif.) using $P<0.05$ as the level of significance.

In dose response studies, rat amylin (Bachem, Torrance, Calif.) dissolved in 0.15M saline, was administered as a 0.1 mL subcutaneous bolus in doses of 0, 0.01, 0.1, 1, 10 or 100 µg 5 minutes before gavage in Harlan Sprague Dawley (non-diabetic) rats fasted 20 hours and diabetic BB rats fasted 6 hours. When subcutaneous amylin injections were given 5 minutes before gavage with phenol red indicator, there was a dose-dependent suppression of gastric emptying (data not shown). Suppression of gastric emptying was complete in normal HSD rats administered 1 µg of amylin, and in diabetic rats administered 10 µg (P=0.22, 0.14). The $ED_{50}$ for inhibition of gastric emptying in normal rats was 0.43 µg (0.60 nmol/kg) ±0.19 log units, and was 2.2 µg (2.3 nmol/kg) ±0.18 log units in diabetic rats.

Amylin (rat or human) and compounds that exhibit amylin-like actions in isolated soleus muscle (including, salmon calcitonin, CGRP, and rat calcitonin) have been observed to dose-dependently inhibit gastric emptying in the present conscious rat model. Adrenomedullin, which has been observed to behave as a CGRP agonist but not as an amylin or calcitonin agonist, does not inhibit gastric emptying at the highest doses (100 µg) used in this model (indicating that inhibition of gastric emptying in this model is unlikely to be mediated by CGRP receptors).

Figure 7:
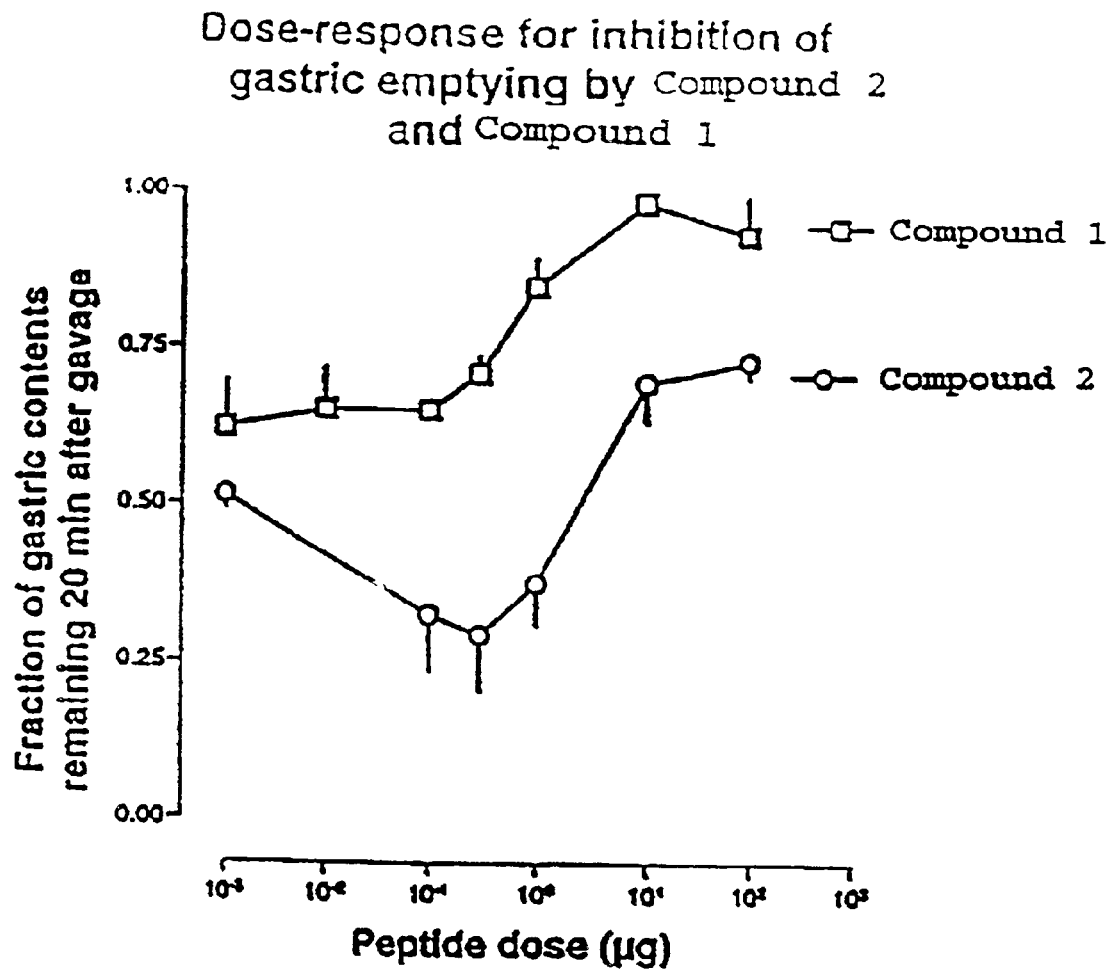
FIG. 7 depicts a dose response curve for the in vivo effects of Compound 1 and Compound 2 on inhibition of gastric emptying in rats.

As shown FIG. 7, amylin and rat calcitonin had similar potencies in inhibiting gastric emptying ($ED_{50}$s of 0.21 and 0.41 µg/rat, respectively; n.s.). Salmon calcitonin was more potent than rat calcitonin in its gastric emptying inhibition effect ($ED_{50}$ 0.12 µg/rat; P<0.03). Both Compound 1 and Compound 2 behaved as potent amylin and calcitonin agonists in inhibition of gastric emptying.

We claim:

1. A compound of the formula:

$X_1$-$X_2$-$X_3$-Leu-$X_4$-Glu-Leu-$X_5$-$X_6$-Leu-Gln-Thr-Tyr-Pro-Arg-Thr-Asn-$X_7$-$Z_3$ [SEQ.ID.NO.27]

wherein:

(a) $X_1$ is
  (i) a group of two amino acid residues selected from the group consisting of Leu-Leu, Val-Leu, Ile-Leu, tert-Leu-Leu, Nle-Leu, and Ala-Thr, and N-acylated derivatives thereof; or
  (ii) the group $Z_1$-Ser-Thr-$Z_2$-Val-Leu [SEQ.ID.NO. 28] wherein $Z_1$ is an amino acid residue selected from the group consisting of Leu, Val, Ile, tert-Leu, Nva, Abu, and Nle or an N-acylated derivative thereof or $Z_1$ is an alkanoyl group; and $Z_2$ is a amino acid residue selected from the group consisting of Ala, Ser, Cys, and Thr;

(b) $X_2$ is an amino acid residue selected from the group consisting of Gly, Glu, Asn or Aib;

(c) $X_3$ is an amino acid residue selected from the group consisting of Arg, Orn, Lys and ε-amidated derivatives thereof;

(d) $X_4$ is a group of two amino acid residues selected from the group consisting of Ser-Gln, Thr-Gln, Ala-Asn and Thr-Asn;

(e) $X_5$ is an amino acid residue selected from the group consisting of His, Aib, Ile, Leu and Val;

(f) $X_6$ is an amino acid residue selected from the group consisting of Arg, Orn and Lys and ε-amidated derivatives thereof;

(g) $X_7$ is a group having 6 amino acid residues selected from the group consisting of
  (i) Thr-Gly-Ser-Asn-Thr-Tyr [SEQ.ID.NO. 29];
  (ii) Thr-Gly-Ser-Gly-Thr-Pro [SEQ.ID.NO. 30];
  (iii) Val-Gly-Ser-Asn-Thr-Tyr [SEQ.ID.NO. 31];
  (iv) Val-Gly-Ser-Gly-Thr-Pro [SEQ.ID.NO. 32]; and (h) $Z_a$ is OH or $NH_2$;

with the proviso that the compound does not have the formula of any of SEQ. ID. NOS. 14 to 26; and pharmaceutically acceptable salts thereof.

2. A compound according to claim 1 wherein $Z_3$ is $NH_2$.

3. A compound according to claim 1 wherein $X_2$ is Gly.

4. A compound according to claim 3 wherein $X_5$ is His or Aib.

5. A compound according to claim 4 wherein $X_4$ is Ser-Gln.

6. A compound according to claim 5 wherein $X_7$ is Thr-Gly-Ser-Asn-Thr-Tyr [SEQ.ID.NO. 29] or Thr-Gly-Ser-Gly-Thr-Pro-$NH_2$ [SEQ.ID.NO. 30].

7. A compound according to claim 6 wherein $X_1$ is $Z_1$-Ser-Thr-$Z_2$-Val-Leu [SEQ.ID.NO.28].

8. A compound according to claim 7 wherein $X_3$ and $X_6$ are ε-amidated with a carboxylic acid having 1 to 8 carbon atoms.

9. A compound according to claim 1 wherein $Z_1$ is an alkanoyl group having 1 to about 10 carbon atoms or Leu.

10. A compound according to claim 9 wherein $Z_2$ is Ala or Cys.

11. A compound according to claim 10 wherein $Z_1$ is an alkanoyl group.

12. A compound according to claim 11 wherein $X_3$ and $X_6$ are formamidated or acetamidated.

13. A compound according to claim 12 wherein $Z_2$ is Ala.

14. A compound according to claim 13 wherein $X_3$ and $X_6$ are Lys(For).

15. A compound according to claim 14 wherein $Z_1$ is 4-methylpentanoyl.

16. A compound according to claim 1 which has an amino acid sequence selected from the group consisting of:

Leu-Ser-Thr-Cys-Val-Leu-Gly-Arg-Leu-Ser-Gln-Glu-Leu-His-Arg-Leu-Gln-Thr-Tyr-Pro-Arg-Thr-Asn-Thr-Gly-Ser-Asn-Thr-Tyr [SEQ.ID.NO. 1];

4-methylpentanoyl-Ser-Thr-Ala-Val-Leu-Aib-Lys(For)-Leu-Ser-Gln-Glu-Leu-Aib-Lys(For)-Leu-Gln-Thr-Tyr-Pro-Arg-Thr-Asn-Thr-Gly-Ser-Gly-Thr-Pro [SEQ.ID.NO. 2];

Ac-Leu-Ser-Thr-Ser-Val-Leu-Gly-Arg-Leu-Ser-Gln-Glu-Leu-His-Arg-Leu-Gln-Thr-Tyr-Pro-Arg-Thr-Asn-Thr-Gly-Ser-Asn-Thr-Tyr [SEQ.ID.NO. 3];

Leu-Ser-Thr-Ala-Val-Leu-Gly-Arg-Leu-Ser-Gln-Glu-Leu-His-Arg-Leu-Gln-Thr-Tyr-Pro-Arg-Thr-Asn-Thr-Gly-Ser-Asn-Thr-Tyr [SEQ.ID.NO. 4];

Leu-Ser-Thr-Ser-Val-Leu-Gly-Arg-Leu-Ser-Gln-Glu-Leu-His-Arg-Leu-Gln-Thr-Tyr-Pro-Arg-Thr-Asn-Thr-Gly-Ser-Asn-Thr-Tyr [SEQ.ID.NO. 5];

Ac-Leu-Ser-Thr-Ala-Val-Leu-Gly-Arg-Leu-Ser-Gln-Glu-Leu-His-Arg-Leu-Gln-Thr-Tyr-Pro-Arg-Thr-Asn-Thr-Gly-Ser-Asn-Thr-Tyr [SEQ.ID.NO. 6];

Ac-Leu-Ser-Thr-Cys-Val-Leu-Gly-Arg-Leu-Ser-Gln-Glu-Leu-His-Arg-Leu-Gln-Thr-Tyr-Pro-Arg-Thr-Asn-Thr-Gly-Ser-Asn-Thr-Tyr [SEQ.ID.NO. 7];

Val-Leu-Aib-Lys(For)-Leu-Ser-Gln-Gl-Leu-Aib-Lys(For)-Leu-Gln-Thr-Tyr-Pro-Arg-Thr-Asn-Thr-Gly-Ser-Asn-Thr-Tyr [SEQ.ID.NO. 8];

Ac-Val-Leu-Aib-Lys(For)-Leu-Ser-Gln-Glu-Leu-Aib-Lys(For)-Leu-Gln-Thr-Tyr-Pro-Arg-Thr-Asn-Thr-Gly-Ser-Asn-Thr-Tyr [SEQ.ID.NO. 9];

4-methylpentanoyl-Ser-Thr-Ala-Val-Leu-Aib-Lys(For)-Leu-Ser-Gln-Glu-Leu-Aib-Lys(For)-Leu-Gln-Thr-Tyr-Pro-Arg-Thr-Asn-Thr-Gly-Ser-Asn-Thr-Tyr [SEQ.ID.NO. 10];

4-methylpentanoyl-Ser-Thr-Cys-Val-Leu-Aib-Lys(For)-Leu-Ser-Gln-Glu-Leu-Aib-Lys(For)-Leu-Gln-Thr-Tyr-Pro-Arg-Thr-Asn-Thr-Gly-Ser-Asn-Thr-Tyr [SEQ.ID.NO. 11];

Ala-Thr-Aib-Lys(For)-Leu-Ala-Asn-Glu-Leu-Aib-Lys(For)-Leu-Gln-Thr-Tyr-Pro-Arg-Thr-Asn-Thr-Gly-Ser-Asn-Thr-Tyr [SEQ.ID.NO. 12];

and

Ac-Ala-Thr-Aib-Lys(For)-Leu-Ala-Asn-Glu-Leu-Aib-Lys(For)-Leu-Gln-Thr-Tyr-Pro-Arg-Thr-Asn-Thr-Gly-Ser-Asn-Thr-Tyr [SEQ.ID.NO. 13].

17. The compound Leu-Ser-Thr-Cys-Val-Leu-Gly-Arg-Leu-Ser-Gln-Glu-Leu-His-Arg-Leu-Gln-Thr-Tyr-Pro-Arg-Thr-Asn-Thr-Gly-Ser-Asn-Thr-Tyr [SEQ.ID.NO. 1].

18. The compound 4-methylpentanoyl-Ser-Thr-Ala-Val-Leu-Aib-Lys(For)-Leu-Ser-Gln-Glu-Leu-Aib-Lys(For)-Leu-Gln-Thr-Tyr-Pro-Arg-Thr-Asn-Thr-Gly-Ser-Gly-Thr-Pro [SEQ.ID.NO. 2].

19. A composition comprising a compound of any of claims 1 to 8 in a pharmaceutically acceptable carrier.

20. A method of treating diabetes in a subject in need of treatment which comprises administering to said subject a therapeutically effective amount of a compound of any of claim 1, 2, 15, 16, 17 or 18.

21. A method according to claim 20 wherein said diabetes is type I diabetes.

22. A method according to claim 20 wherein said diabetes is type II diabetes.

23. A method of beneficially regulating gastrointestinal motility in a subject comprising administering to said subject a therapeutically effective amount of a compound of any of claim 1, 2, 15, 16, 17 or 18.

24. A method according to claim 23 wherein said beneficial regulation of gastrointestinal motility comprises delaying gastric emptying.

25. A method of treating a disorder selected from the group consisting of: impaired glucose tolerance; postprandial hyperglycemia; obesity; and Syndrome x; in a subject in need of treatment which comprises administering to said subject a therapeutically effective amount of a compound of any of claim 1, 2, 15, 16, 17 or 18.

* * * * *

UNITED STATES PATENT AND TRADEMARK OFFICE
CERTIFICATE OF CORRECTION

PATENT NO. : 6,936,584 B1
DATED : August 30, 2005
INVENTOR(S) : Nigel R.A. Beeley, Kathryn Prickett and Kevin Beaumont It is certified that error appears in the above-identified patent and that said Letters Patent is hereby corrected as shown below:

Title page,
Item [86], PCT No., "Jul. 17, 2001" should be -- Jul. 16, 2001 --.

Column 46,
Line 7, "8" should be -- 18 --.

Signed and Sealed this

Twenty-fourth Day of January, 2006

JON W. DUDAS
*Director of the United States Patent and Trademark Office*